Figure 1C:
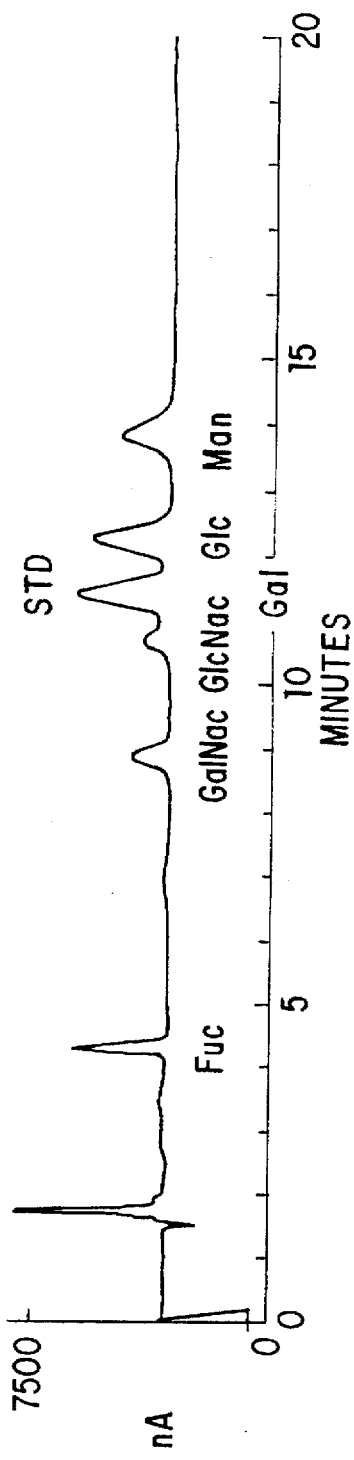

US005679564A

United States Patent [19]

Pace et al.

[11] Patent Number: 5,679,564
[45] Date of Patent: Oct. 21, 1997

[54] METHODS FOR PRODUCING ENHANCED ANTIGENIC CAMPYLOBACTER BACTERIA AND VACCINES

[75] Inventors: John Lee Pace, Germantown; Richard Ives Walker, Gaithersburg; Steven Michael Frey, Germantown, all of Md.

[73] Assignee: Antex Biologics, Inc., Gaithersburg, Md.

[21] Appl. No.: 538,545

[22] Filed: Oct. 3, 1995

Related U.S. Application Data

[63] Continuation-in-part of Ser. No. 318,409, Oct. 5, 1994, abandoned.

[51] Int. Cl.[6] .......................... A01N 63/00; A61K 39/38; A61K 45/00; C12N 1/20

[52] U.S. Cl. ................. 435/252.1; 424/93.4; 424/184.1; 424/282.1

[58] Field of Search ................................ 435/252.1, 822; 424/93.4, 184.1, 282.1

[56] References Cited

U.S. PATENT DOCUMENTS 5,459,041 10/1995 Blaser .................................... 435/7.21

FOREIGN PATENT DOCUMENTS

WO 93/22423 11/1993 WIPO .

OTHER PUBLICATIONS

Andrews & Maurelli, 1992, "*mxiA of Shigella flexneri* 2a, which facilitates export of invasion plasmid antigens, encodes a homolog of the low–calcium–response protein, LcrD, of *Yersinia pestis.*" *Infect. Immun.* 60:3287–3295.

Baqar et al., 1995, "Immunogenicity and protective efficacy of a prototype *Campylobacter* killed whole–cell vaccine in mice." *Infect. Immun.* 63:3731–3735.

Bell & Manning, 1990, "A domestic ferret model of immunity to *Campylobacter jejuni*– induced enteric disease." *Infect. Immun.* 58:1848–1852.

Blaser & Gotschilch, 1990, "Surface array protein of *Campylobacter fetus.*" *J. Biol. Chem.* 265:14529–14535.

Caldwell et al., 1983, "Simple adult rabbit model for *Campylobacter jejuni* enteritis." *Infect. Immun.* 42:1176–1182.

Chen et al., 1992, "Immunization against gastric helicobacter infection in a mouse/*Heliocobacter felis* model." *Lancet* 339:1120–1121.

Durham et al., 1994, *94th Am. Soc. Microbiol.* Abstract P–96, p. 386.

Field et al., 1993, "Characteristics of an avirulent *Campylobacter jejuni* strain and its virulence–enhanced variants." *J. Med. Microbiol.* 38:293–300.

Gilmour et al., 1991, "Vaccine containing iron–regulated proteins of *Pasteurella haemolytica* A2 enhances protection against experimental pasteurellosis in lambs." *Vaccine* 9:137–140.

Grant et al., 1993, "Role of flagella in adherence, internalization, and translocation of *Campylobacter jejuni* in non-polarized and polarized epithelial cell cultures." *Infect. Immun.* 61:1764–1771.

Hale et al., 1985, "Identification and antigenic characterization of virulence–associated, plasmid–coded proteins of *Shigella* spp. and enteroinvasive *Escherichia coli.*" *Infect. Immun.* 50:620–629.

High et al., 1992, "IpaB of *Shigella flexneri* causes entry into epithelial cells and escape from the phagocytic vacuole." *EMBO J.* 11:1991–1999.

Konkel et al., 1993, *J. Infect. Dis.* 168:948–954.

Levenson et al., 1988, "Parental immunization with *Shigella* ribosomal vaccine elicits local Ig A response and primes for mucosal memory." *Arch. Allergy Appl. Immunol.* 87:25–31.

J. Mekalanos, 1992, *J. Bacteriol.* 174:1–7.

Panigrahi et al., 1992 *Infect. Immun.* 60:4938–4944.

Pavlovskis et al., 1992, "Significance of flagella in colonization resistance of rabbits immunized with *Campylobacter* spp.." *Infect. Immun.* 59:2259–2264.

S.M. Payne, 1989, *Mol. Microbiol.* 3:1301–1306.

Payne & Finkelstein, 1977, "Imferon agar: Improved medium for isolation of pathogenic *Nesseria.*" *J. Clin. Microbiol.* 6:293–297.

Pope & Payne, 1993, *93rd Am. Soc. Microbiol.* Abstract B–147.

Robbins et al., 1991, "O–Specific side–chain toxin–protein conjugates as parentaeral vaccines for the prevention of shigellosis and related diseases." *Rev. Inf. Dis.* 13:S362–365.

H.W. Yoder, 1989, "Congo red binding by *Escherichia coli* isolates from chickens." *Avian Dis.* 33:502–505.

*Primary Examiner*—David M. Naff
*Assistant Examiner*—Deborah Ware
*Attorney, Agent, or Firm*—Pennie & Edmonds

[57] ABSTRACT

Methods using in vitro processes are disclosed for inducing or enhancing expression of enteric bacterial antigens or virulence factors. The methods, therefore, produce antigenically enhanced enteric bacteria. Also disclosed are methods for using the antigenically enhanced bacteria, as well as vaccines containing the enteric bacteria. Specifically, a whole enteric bacteria or components thereof are provided by Campylobacter species. In addition to this species there are other enteric bacteria, such as *Helicobacter pylori*, which are useful for inducing or enhancing expression of enteric bacterial antigens and/or virulence factors.

12 Claims, 11 Drawing Sheets

Lane 1 = BHI culture
Lane 2 = BHI + 0.8% oxgall culture
Lane 3 = BHI + 0.1% DOC culture
Lane 4 = Surface extract of BHI culture
Lane 5 = Surface extract of BHI-DOC culture Lane 1 = Fermentor culture (enhc.)
Lane 2 = Flask culture (conv.)
Lane 3 = Flask culture (enhc.)

METHODS FOR PRODUCING ENHANCED ANTIGENIC CAMPYLOBACTER BACTERIA AND VACCINES

This application is a continuation-in-part of application Ser. No. 08/318,409, filed Oct. 5, 1994 now abandoned.

TABLE OF CONTENTS
1 FIELD OF THE INVENTION
2 BACKGROUND OF THE INVENTION
3 SUMMARY OF THE INVENTION
4 BRIEF DESCRIPTION OF THE DRAWINGS
5 DETAILED DESCRIPTION OF THE INVENTION
6 EXAMPLES: METHODS FOR PRODUCING ENHANCED ANTIGENIC BACTERIA
7 EXAMPLES: ENHANCED ANTIGENIC BACTERIA
8 EXAMPLES: VACCINE EFFICACY
9 EXAMPLE: MECHANISM OF ANTIGENIC ALTERATION OR ENHANCEMENT BY DOC
10 EXAMPLE: DOC INDUCES ENHANCED SEROTYPE AND SPECIES IMMUNO-CROSS REACTIVITY OF CAMPYLOBACTER JEJUNI
11 EXAMPLE: ADDITIONAL EXPERIMENTS OF VACCINE EFFICACY OF CAMPYLOBACTER
12 EXAMPLES: DOC ENHANCED INVASIVENESS, CONGO RED BINDING AND IMMUNO-CROSS REACTIVITY OF SHIGELLA
13 EXAMPLE: VACCINE EFFICACY OF SHIGELLA
14 EXAMPLE: FACTORS THAT AFFECT THE ADHESIVENESS OF H. PYLORI TO ANIMAL CELLS
15 EXAMPLE: VACCINE EFFICACY OF HELICOBACTER GROWN ACCORDING TO THE METHODS OF THE PRESENT INVENTION
16 DEPOSIT OF MICROORGANISM

1 FIELD OF THE INVENTION

This invention relates generally to in vitro methods for including or enhancing expression of enteric bacterial antigens and or virulence factors thereby producing antigenically enhanced enteric bacteria, to methods for using antigenically enhanced enteric bacteria and to vaccines comprising antigenically enhanced enteric bacteria.

2 BACKGROUND OF THE INVENTION

It is widely recognized that bacteria cultured in vitro using conventional media and conditions express characteristics that are different from the characteristics expressed during growth in their natural habitats, which includes in vivo growth of normal microflora or pathogens in an animal host. Therefore, such in vitro grown pathogenic bacteria might not be good for use as vaccine components. However, if it were possible to define conditions that trigger or enhance expression of virulence factors, relevant physiology, or antigens including outer-surface antigens then important products and therapeutics (e.g., new antigens for vaccines, new targets for antibiotics, and novel bacterial characteristics for diagnostic applications) could be rapidly identified.

Several environmental factors have been identified which influence expression of virulence determinants in bacteria (Mekalanos, J. J., J. Bacteriol. 174:1–7, 1992). For instance, there is a long history of research on the relationship between iron and virulence of bacteria, in particular Shigella (Payne, Mol. MicroBiol., 3:1301–1306, 1989), Neisseria (Payne and Finkelstein, J. Clin. Microbiol., 6:293–297, 1977) and Pasteurella (Gilmour, et al., Vaccine, 9:137–140, 1991).

Other environmental signals that have been shown to control the expression of coordinately regulated virulence determinants of a wide variety of bacteria in plants and animals include phenolic compounds, monosaccharide, amino acids, temperature, osmolarity, and other ions (Mekalanos, J. Bacteriol., 174:1–7, 1992).

Bacterial pathogens that enter an animal host through the intestine (i.e., oral route) encounter numerous host environment components and conditions that may affect bacterial physiology and expression of virulence factors. These components and conditions include bile, bile acids or salts, stomach pH, microaerophillic conditions (the intestine has high $CO_2$, and low $O_2$), osmolarity and many others yet undefined. Invasive enteric pathogens require de novo protein synthesis to accomplish internalization (Headley and Payne, Proc. Natl. Acad. Sci., USA, 87:4179–4183, 1990). Therefore, bacteria may optimally produce these invasive factors only in response to certain environmental signals not ordinarily present in vitro. This hypothesis is supported by the recent report that antisera raised against conventionally grown C. jejuni had only a marginal effect on blocking in vitro internalization (Konkel, et al., J. Infect. Dis., 168:948–954, 1993). However, immunization of rabbits with extracts of Campylobacter grown in the presence of epithelial cell monolayers, a condition enhancing invasiveness, resulted in production of an antiserum that markedly inhibited the internalization of the bacteria.

Researchers have been studying growth of bacteria in the intestinal environment to identify relevant virulence factors. For example, Campylobacter strain 81–176 grown in rabbit ileal loops expresses proteins not expressed under conventional laboratory in vitro culture conditions (Panigrahi, et al., Infect. Immun., 60:4938–4944, 1992). New or enhanced synthesis of proteins has been seen in Campylobacter cultivated with INT 407 cell monolayers as compared to bacteria cultured in the absence of the epithelial cells (Konkel, et al., J. Infect. Dis., 168:948–954, 1993). Furthermore, these changes were temporally associated with increased invasiveness of C. jejuni. Other changes such as cellular morphology, loss of flagella, expression of a new outer membrane protein and alteration in cell-surface carbohydrates were induced or enhanced in an avirulent strain of C. jejuni when passed intravenously and chorioallantoically through chick embryos (Field, et al., J. Med. Microbiol., 38:293–300, 1993).

Other intestinal components, such as bile acids or salts, are known to be inhibitory for some bacteria, but the bile acids may play another role by affecting virulence expression by the bacterium.

Pope and Payne (93rd Am. Soc. Microbiol., B-147, 1993) reported that Shigella flexneri cultured in broth containing sodium chenodeoxycholate demonstrated 3 to 5-fold enhanced infectivity of HeLa cell monolayers. They reported, however, that other bile salts and detergents including cholate, glycocholate, taurodeoxycholate, the CHAPS series, digitonin and Triton X100 and sodium salts thereof, had no effect on the invasiveness of S. flexneri. Moreover, their broth containing chenodeoxycholate also had no effect on the invasiveness of E. coli or other avirulent strains of Shigella.

Synthesis of new proteins by S. flexneri is also induced by altering pH, temperature and ionic composition of the growth medium (Mekalanos, J. Bacteriol., 174:1–7, 1992).

PCT application publication number WO 93/22423, published Nov. 11, 1993, discloses methods for growing bacteria on lipids, such as phosphatidylserine, or mucus and for the isolation of proteins whose expression is enhanced by growth in the presence of phosphatidylserine. This reference neither discloses nor suggests methods of the present invention for producing enteric bacteria having enhanced virulence or antigenic properties.

Vaccines against many enteric pathogens, such as Campylobacter and Shigella, are not yet available but the epidemiology of these disease agents makes such vaccines an important goal. Shigellosis is endemic throughout the world and in developing countries it accounts for about 10 percent of the 5 million childhood deaths annually due to diarrhea. Campylobacter, although only recently identified as an enteric pathogen is now recognized as one of the major causes of diarrheal disease in both the developed and underdeveloped countries. An estimated 400 to 500 million Campylobacter diarrheas occur yearly, and over 2 million cases occur in the United States.

Shigellosis is a consequence of bacterial invasion of the colonic mucosa. The invasion is associated with the presence of a plasmid found in all invasive isolates (Sansonetti et al., *Infect. Immun.*, 35:852–860, 1982). A fragment of this plasmid contains the invasion plasmid antigen (Ipa) genes, Ipa A, –B, –C, and –D. Ipa B, –C, and –D proteins are essential for the entry process (Baudry et al., *J. Gen. Microbiol.*, 133:3403–3413, 1987).

Ipa proteins are logical vaccine candidates although their protective efficacy has not been clearly established. Ipa B and Ipa C are immunodominant proteins (Hale, et al., *Infect. Immun.*, 50:620–629, 1985). Furthermore, the 62 kDa Ipa B protein (the invasin that initiates cell entry and functions in the lysis of the membrane-bound phagocytic vacuole) (High, et al., *EMBO J.*, 11:1991–1999, 1992) is highly conserved among Shigella species. The prolonged illness observed in malnourished children who have no significant mucosal antibody to Shigella Ipa suggests that the presence of mucosal antibody to Ipa may limit the spread and severity of infection.

Though a number of vaccine candidates for Shigella have been tested in animals and humans, a successful one has not been found. In spite of the potential significance of Ipa proteins in virulence, most vaccine candidates developed against shigellosis are based on the lipopolysaccharide antigen, which carries the serotype-specific determinants. A parenterally administered polysaccharide-protein conjugate vaccine has also been developed, but is yet to show significant protection in animals (Robbins et al., *Rev. Inf. Dis.*, 13:S362–365, 1991). A similarly administered ribosomal vaccine does induce mucosal immunity, but its protective efficacy remains to be demonstrated (Levenson et al., *Arch. Allergy Appl. Immunol.*, 87:25–31, 1988).

The pathogenesis of Campylobacter infections is not as well understood as that of Shigella infections. Cell invasion studies in vitro (Konkel, et al., *J. Infect. Dis.*, 168:948–954, 1993) and histopathologic examinations (Russell, et al., *J. Infect. Dis.*, 168:210–215, 1993) suggest that colonic invasion is also important. This conclusion is consistent with the observation that diarrhea caused by Campylobacter may be severe and associated with blood in the stool. These activities may be associated with the immunodominant 62 kDa flagellin protein. A recent report indicates that the presence of flagella is essential for Campylobacter to cross polarized epithelial cell monolayers (Grant et al., *Infect. Immun.*, 61:1764–1771, 1993).

No specific Campylobacter antigens have been established as protective. However, the low molecular weight (28–31 kDa) proteins, or PEB proteins, and the immunodominant flagellar protein are thought to hold promise in this regard (Pavlovskis et al., *Infect. Immun.*, 59:2259–2264, 1992; Blaser and Gotschilch, *J. Bio. Chem.*, 265:14529–14535, 1990). The importance of the flagellar protein is indicated by its association with colonization of the intestine and with the cross-strain protection against infection within Lior subgroups (Pavlovskis et al., *Infect. Immun.*, 59:2259–2264, 1992). However, a flagella protein based Campylobacter vaccine may have to include the flagella protein antigen from the 8–10 most clinically relevant Lior serogroups.

Therefore, objects of the present invention include 1) in vitro culture conditions for culturing or treating enteric bacteria which optimally induce or enhance invasive activities and/or certain cellular characteristics including cell surface characteristics; 2) correlated altered invasiveness or cellular characteristics including surface characteristics with changes in antigenic profiles; 3) increased virulence of these organisms in small animal models; and 4) antisera against organisms with enhanced invasiveness or altered characteristics including surface characteristics that are more effective in neutralizing live organisms used for in vitro or in vivo challenges than antisera prepared against conventionally grown bacteria. This invention addresses these needs and others.

None of the references discussed above teach or suggest the in vitro methods of the present invention nor the vaccines of the present invention comprising antigenically enhanced enteric bacteria. Citation or identification of any reference in this section or any other section of this application shall not be construed as indicative that such reference is available as prior art to the invention.

3 SUMMARY OF THE INVENTION

This invention provides defined culture conditions and components incorporated into growth media of enteric bacteria to induce or enhance the presence of virulence factors and other antigens. Preferably, such antigens are immunogenic. More preferably, such immunogenic antigens correlate with indices of virulence.

Enteric bacteria are grown in the presence of conditions and components simulating certain in vivo conditions to which the organisms are exposed in nature. Methods of the present invention produce antigenically enhanced enteric bacteria with phenotypic changes such as increased total protein per cell, new or increased individual proteins, altered or increased surface carbohydrates, altered surface lipopolysaccharides, increased adhesive ability, increased invasive ability and/or increased intracellular swarming. Moreover, methods of the present invention are adaptable to practical scale-up fermentations for commercial uses.

Said antigenically enhanced enteric bacteria can be used to produce protective vaccines, such as inactivated whole cell or subunit vaccines, or for diagnostic purposes such as for the production of antibodies and detection of pathogenic enteric bacteria or to produce antibiotics. Further, the antibodies induced by the enhanced enteric bacteria of the present invention may be used as passive vaccines.

Therefore, an object of the present invention is a method for producing enteric bacteria selected from the group consisting of Campylobacter spp., Yersinia spp., Helicobacter spp., Gastrospirillum sp., Bacteroides spp., Klebsiella spp., Enterobacter spp., Salmonella spp., Shigella spp., Aeromonas spp., Vibrio spp., Clostridium spp., Enterococcus spp. and *Escherichia coli*, having enhanced antigenic properties comprising: growing enteric bacteria in vitro with a combination of conditions including: a) 0.05% to 3% bile or 0.025% to 0.6% of one or more bile acids or salts thereof, at a temperature between 30° C. and 42° C., until a growth phase at about early log phase, between early log and stationary phases, or at about stationary phase, in air or microaerophillic conditions, such as 5% to 20% $CO_2$ with 80% to 95% air, 5% to 20% $CO_2$ with 80% to 95% $N_2$; or 5% to 10% $O_2$, 10% to 20% $CO_2$, with 70% to 85% $N_2$; and optionally in the presence of a divalent cation chelator, such as, but not limited to 0 to 100 µM, preferably 25 µM, of BAPTA/AM, 0 to 10 mM of EGTA, and 0 to 100 µM of EGTA/AM; or b) as in a) except in the presence of a divalent cation chelator, such as 1.0 to 100 µM, preferably 25 µM, of BAPTA/AM, 0.5 to 10 mM of EGTA, or 1 to 100 µM of EGTA/AM, and without any bile, bile acids or bile salts.

According to the present invention, concentrations of any individual bile acid or salt thereof include 0.025% to 0.6%, preferably 0.05% to 0.5%, more preferably 0.05% to 0.2%, most preferred is 0.05% or 0.1%. Preferred are methods wherein said bile acid or salt thereof comprises deoxycholate or glycocholate.

A further object of the invention is enteric bacteria selected from the group consisting of: Campylobacter spp, Helicobacter spp., Gastrospirillum spp., Bacteroides spp., Klebsiella spp., Enterobacter spp., Salmonella spp., Shigella spp., Aeromonas spp., Vibrio spp., Clostridium spp., Enterococcus spp. and *Escherichia coli*, wherein said enteric bacteria are grown in vitro under a combination of conditions to promote enhanced antigenic properties, said conditions comprising: a) 0.05% to 3% bile or 0.025% to 0.6% of one or more bile acids or salts thereof, at a temperature between 30° C. and 42° C., until a growth phase at about early log phase, between early log and stationary phases, or at about stationary phase; in air or under microaerophillic conditions, such as 5% to 20% $CO_2$ with 80% to 95% air, 5% to 20% $CO_2$ with 80% to 95% $N_2$, or 5% to 10% $O_2$ with 10% to 20% $CO_2$, with 70% to 85% $N_2$; and optionally a divalent cation chelator, such as, but not limited to 0 to 100 µM, preferably 25 µM, of BAPTA/AM, 0 to 10 mM of EGTA, and 0 to 100 µM of EGTA/AM, or b) as in a) except in the presence of a divalent cation chelator, such as 1.0 to 100 µM, preferably 25 µM, of BAPTA/AM, 0.5 to 10 mM of EGTA, 1.0 to 100 µM of EGTA/AM, and without any bile, bile acids or bile salts.

Another object of the invention is a vaccine comprising a whole enteric bacteria or components thereof, selected from the group consisting of: Campylobacter spp., Yersinia spp., Helicobacter spp., Gastrospirillum spp., Bacteroides spp., Klebsiella spp., Enterobacter spp., Salmonella spp., Shigella spp., Aeromonas spp., Vibrio spp., Clostridium spp., Enterococcus spp. and *Escherichia coli*, or an immunogenic fragment or derivative thereof, having enhanced antigenic properties; and optionally a pharmaceutically acceptable carrier or diluent.

Preferred is the vaccine comprising whole, inactivated antigenically enhanced enteric bacteria. A further object of the invention is a vaccine further comprising an adjuvant.

A further object of the present invention is directed to antibodies (including but not limited to antisera, purified IgG or IgA antibodies, Fab fragment, etc.) which are capable of specifically binding to at least one antigenic determinant of an enteric bacteria of the present invention. Such polyclonal and monoclonal antibodies are useful as immunoassay reagents for detecting enteric bacteria in an animal or biological sample therefrom. The polyclonal and monoclonal antibodies of the present invention are also useful as passive vaccines for use in protecting against enteric bacteria infections and diseases.

A further object of the invention is an in vitro method for assaying potential antimicrobial agents comprising the steps of contacting enteric bacteria having enhanced antigenic properties selected from the group consisting of: Campylobacter spp., Yersinia spp., Helicobacter spp., Gastrospirillum spp., Bacteroides spp., Klebsiella spp., Enterobacter spp., Salmonella spp., Shigella spp., Aeromonas spp., Vibrio spp., Clostridium spp., Enterococcus spp. and *Escherichia coli*, with said potential agents and assaying the bacteriocidal or bacteriostatic effects.

Still a further object of the invention is an in vitro method for detecting a host's production of antibodies or for the detection of enteric bacteria in an animal or biological sample therefrom, comprising the steps of contacting a biological sample from a host with enteric bacteria of the present invention having enhanced antigenic properties selected from the group consisting of: Campylobacter spp., Yersinia spp., Helicobacter spp., Gastrospirillum spp., Bacteroides spp., Klebsiella spp., Enterobacter spp., Salmonella spp., Shigella spp., Aeromonas spp., Vibrio spp., Clostridium spp., Enterococcus spp. and *Escherichia coli*, antigens thereof or antibodies thereto and screening for antibody:antigen interactions.

Another object of the present invention relates to a diagnostic kit for detecting a host's production of antibodies to enteric bacteria or for detecting enteric bacteria, comprising enteric bacteria having enhanced antigenic properties selected from the group consisting of: Campylobacter spp., Yersinia spp., Helicobacter spp., Gastrospirillum spp., Bacteroides spp., Klebsiella spp., Enterobacter spp., Salmonella spp., Shigella spp., Aeromonas spp., Vibrio spp., Clostridium spp., Enterococcus spp. and *Escherichia coli*, or antibodies thereto and all other essential kit components.

Preferred enteric bacteria that the various aspects of the present invention relate to are *Campylobacter jejuni, Campylobacter coli, Yersinia enterocolitica, Yersinia pestis, Yersinia pseudotuberculosis, Escherichia coli, Shigella flexneri, Shigella sonnei, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Klebsiella pneumoniae, Enterobacter cloacae*, and *Enterococcus faecalis*. Preferred *Escherichia coli* include but are not limited to entero-toxic, entero-hemorrhagic, entero-invasive, entero-pathogenic or other strains.

The present invention is based, in part, on the surprising discovery that antigenically enhanced enteric bacteria of the invention induce immune responses that are cross-protective against a broader range of strains or serotypes of the same bacterial species than that induced by the same enteric bacteria but grown using conventional culturing conditions. In at least one instance, the immune response induced by the antigenically enhanced enteric bacteria of the invention is cross-protective against a different species of enteric bacteria.

4 BRIEF DESCRIPTION OF THE DRAWINGS

Figure 1B:
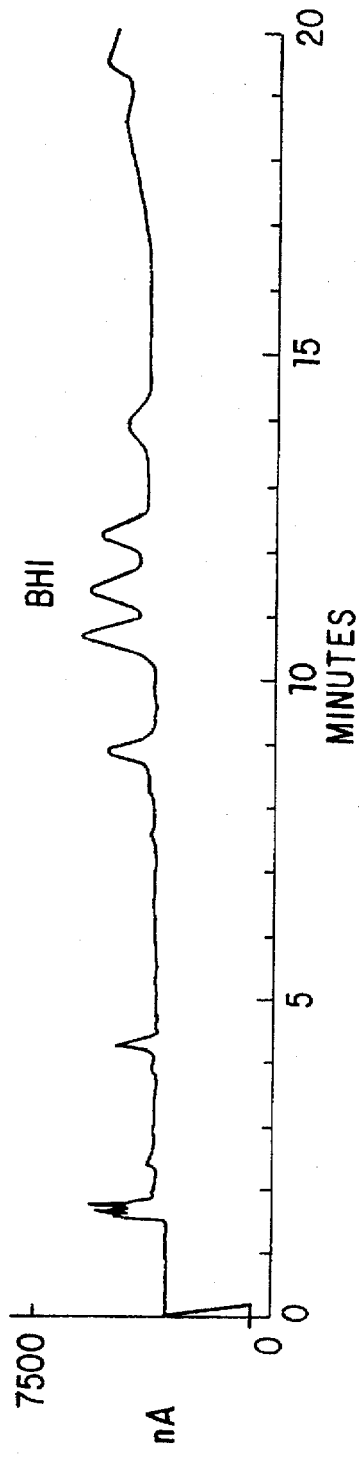
Figure 1A:
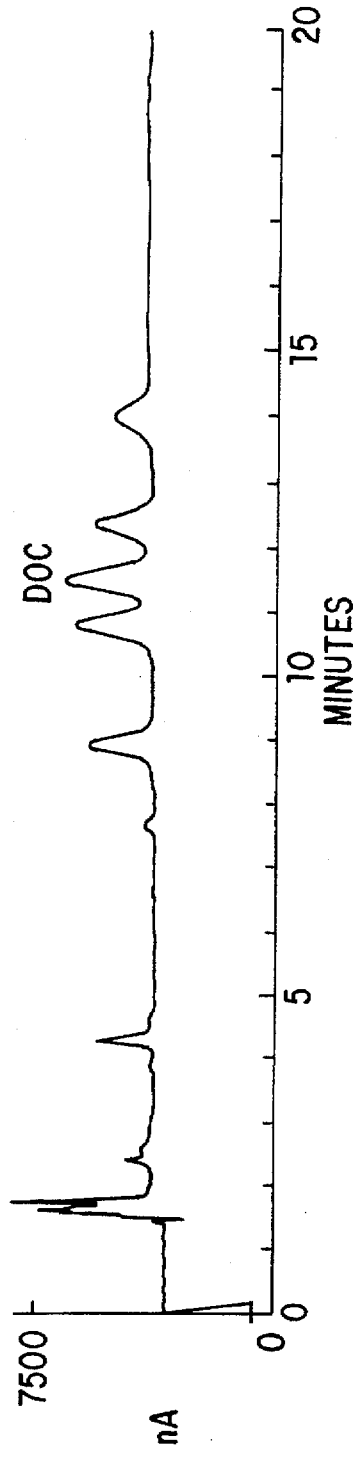

FIGS. 1A, 1B and 1C graphically depict the results of high-performance liquid chromatography of monosaccharides from surface extract hydrolysates of *C. jejuni* 81–176. FIG. 1A: Standards: Fucose "Fuc", N-acetyl-galactosamine "GalNac", N-acetyl-glucosamine "GlcNac", galactose "Gal", glucose "Glc", Mannose "Man". FIG. 1B: surface extract of conventionally grown bacteria "BHI". FIG. 1C: surface extracts of bacteria grown according to methods of the present invention "DOC".

Figure 2:
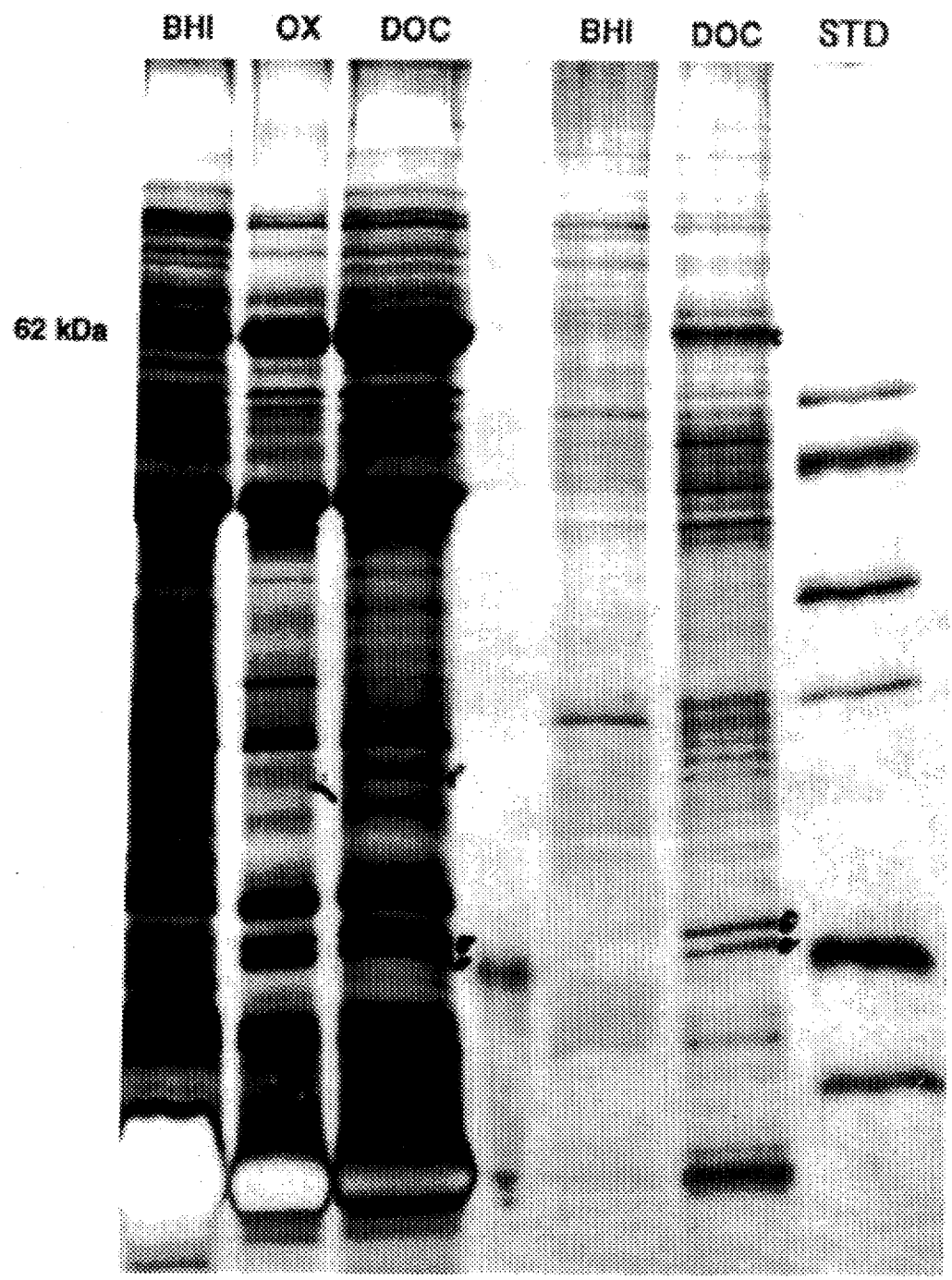

FIG. 2 pictorially depicts the results of sodium dodecyl sulfate-polyacrylamide gel electrophoresis (SDS-PAGE) showing a comparison of proteins of whole cell (columns 1, 2 and 3) or surface extracts (col 5 and 6) of *C. jejuni* 81–176 conventionally grown "BHI" or grown according to methods of the present invention (0.8% Oxgall bile acids "OX" or 0.1% deoxycholate "DOC").

Figure 3:
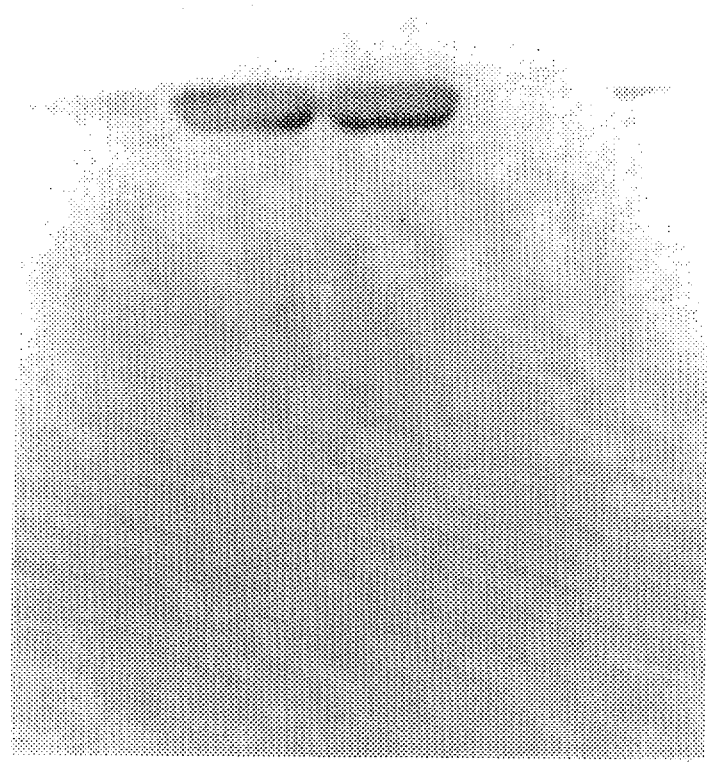

FIG. 3 pictorially depicts the results of western blot analysis showing a comparison of proteins bound by ferret IgA-containing mucus produced by infection with whole cell *C. jejuni* 81–176. Whole cell *C. jejuni* 81–176 conventionally grown, "1"; or whole cell *C. jejuni* 81–176 grown according to methods of the present invention: 0.8% Oxgall bile acids, "2", or 0.1% deoxycholate, "3"; or surface extracts of *C. jejuni* 81–176 conventionally grown, "4"; or surface extracts of *C. jejuni* 81–176 grown according to methods of the present invention, 0.1% deoxycholate, "5".

Figure 4:
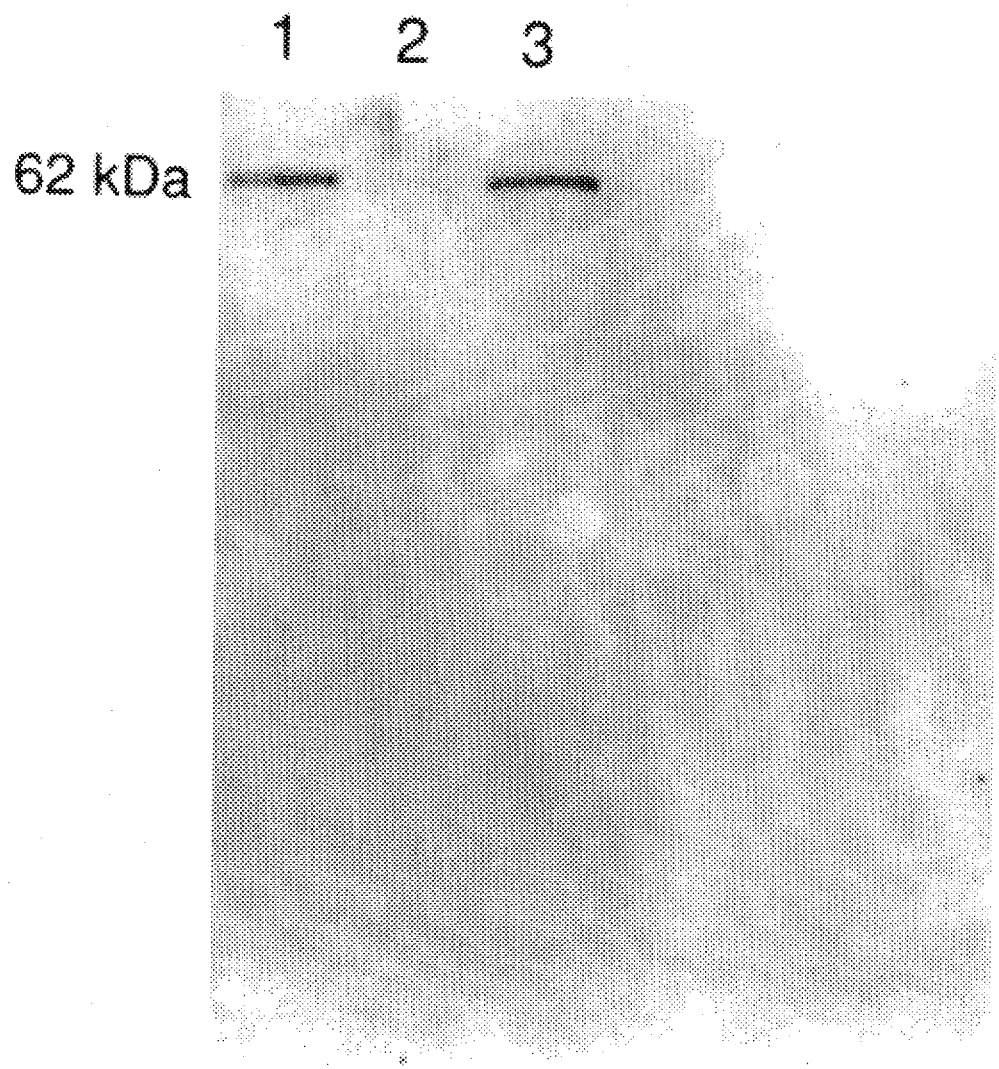

FIG. 4 pictorially depicts the results of western blot analysis showing a comparison of proteins bound by flagellin-specific monoclonal antibody 72c from whole cell *C. jejuni* 81–176 which were grown according to methods of the present invention, "3"; conventionally grown, "2"; or grown in a fermentor according to methods of the present invention, "1".

Figure 5:
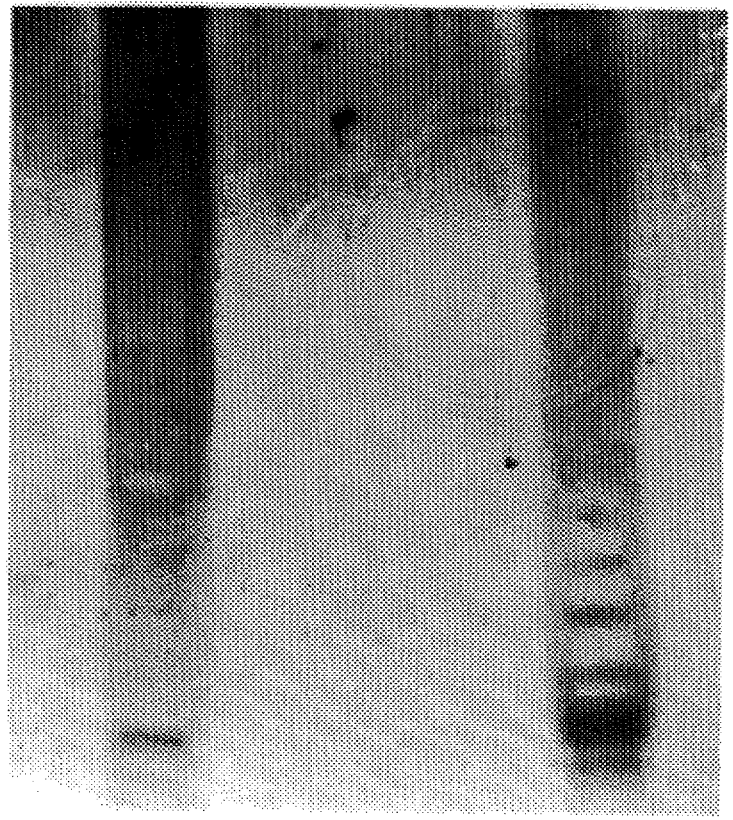

FIG. 5 pictorially depicts the results of SDS-PAGE showing a comparison of lipopolysaccharides (LPS) of whole cell *S. flexneri* 2457T conventionally grown, column "1", or grown according to methods of the present invention, 0.1% deoxycholate, column "2".

Figure 6:
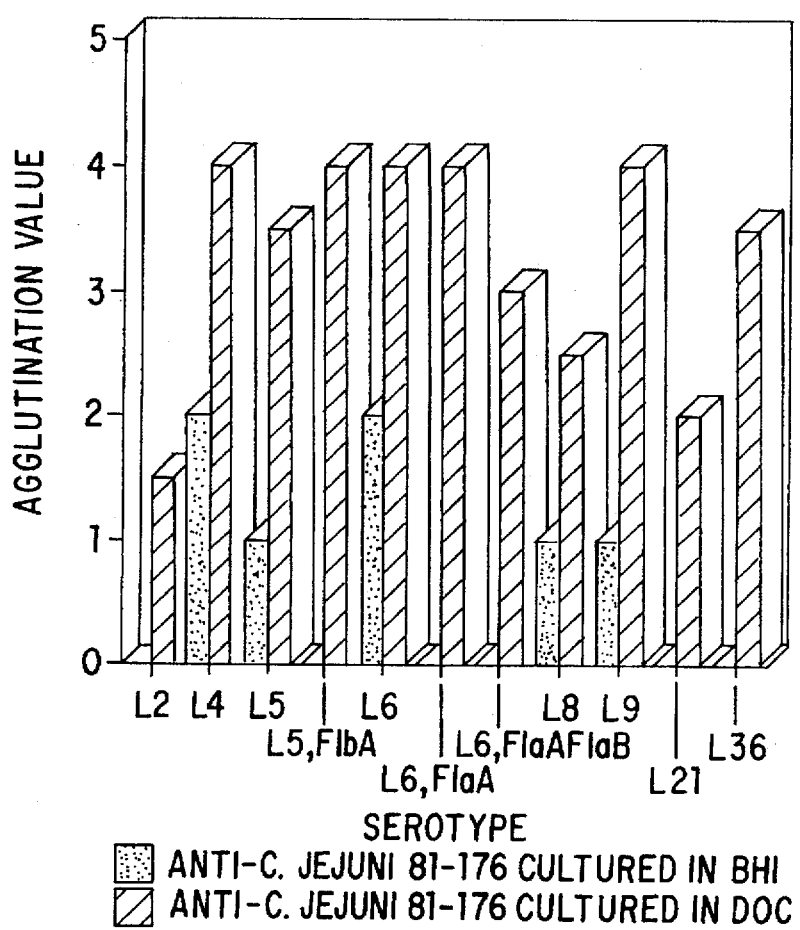

FIG. 6 graphically depicts the enhancement of immunocross reactivity of *C. jejuni* grown according to methods of the present invention. *C. jejuni* 81–176 cells grown conventionally or according to methods of the invention as exemplified in Example 5 (DOC) were used to induce antibodies. The agglutination activity of the two types of antibodies (i.e., anti-*C. jejuni* 81–176 cultured in BHI and anti-*C. jejuni* 81–176 cultured in DOC) against various *C. jejuni* serotypes are shown. See Example 32 in Section 9 for details.

Figure 7A:
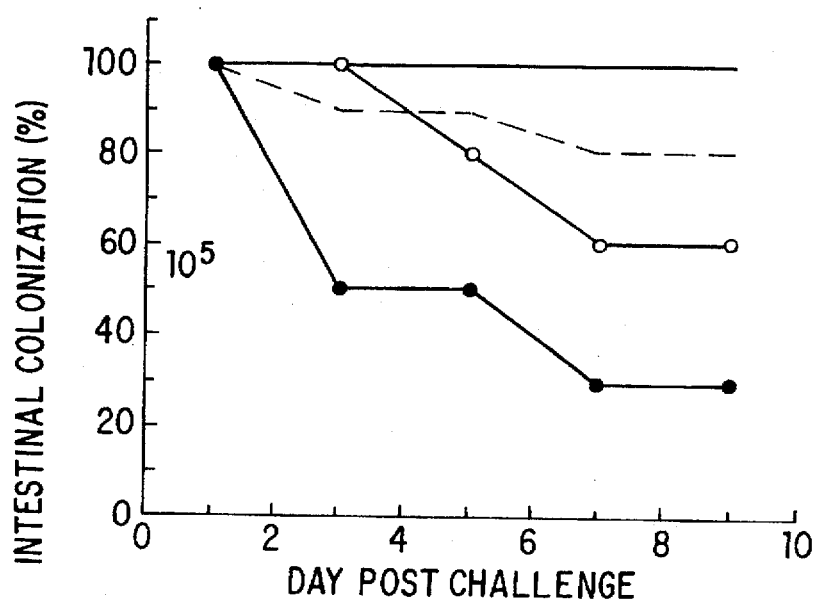
Figure 7B:
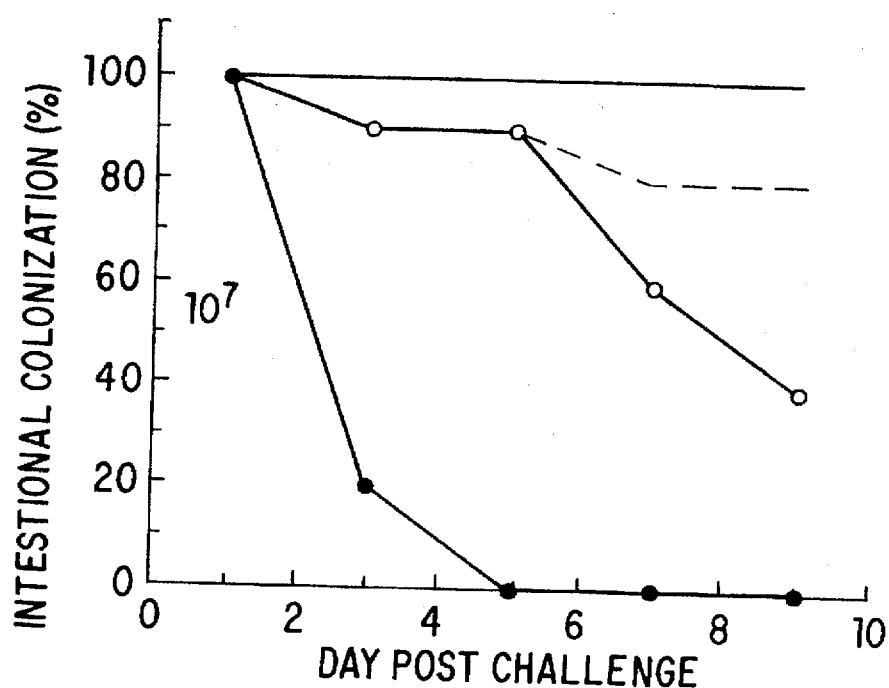
Figure 7C:
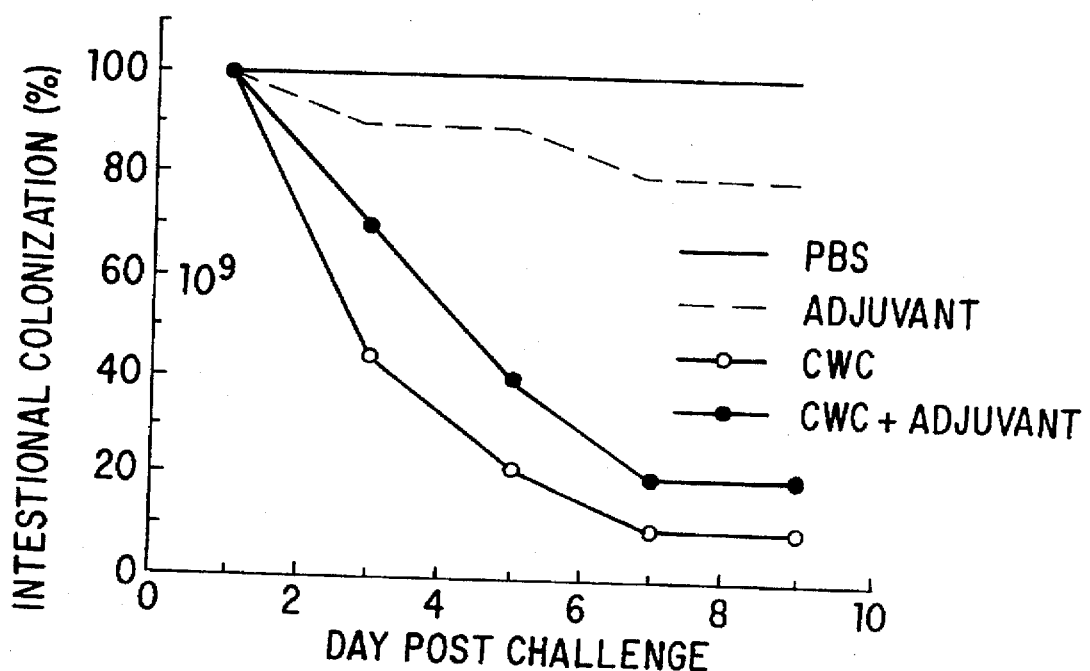

FIGS. 7A, 7B and 7C graphically depict the efficacy of a vaccine comprising inactivated *C. jejuni* 81–176 whole cells in protecting mice against a nasally delivered challenge of live *C. jejuni* 81–176 cells. Mice were vaccinated with phosphate buffered saline (PBS; solid line), PBS plus LT adjuvant (Adjuvant; dash line), formalin-inactivated *C. jejuni* 81–176 whole cells that were grown and harvested according to Example 5 without adjuvant (CWC; open circle/solid line) or with LT adjuvant (CWC+Adjuvant; solid circle/solid line). The vaccine efficacies was examined using the intestinal colonization assay. FIG. 7A (top panel) shows the results of the protection afforded by the vaccinations using three oral doses of $10^5$ inactivated bacterial particles per dose. FIG. 7B (middle panel) shows the results of the protection afforded by the vaccinations using three oral doses of $10^7$ inactivated bacterial particles per dose. FIG. 7C (bottom panel) shows the results of the protection afforded by the vaccinations using three oral doses of $10^9$ inactivated bacterial particles per dose. See Example 34 in Section 11 for details.

Figure 8A:
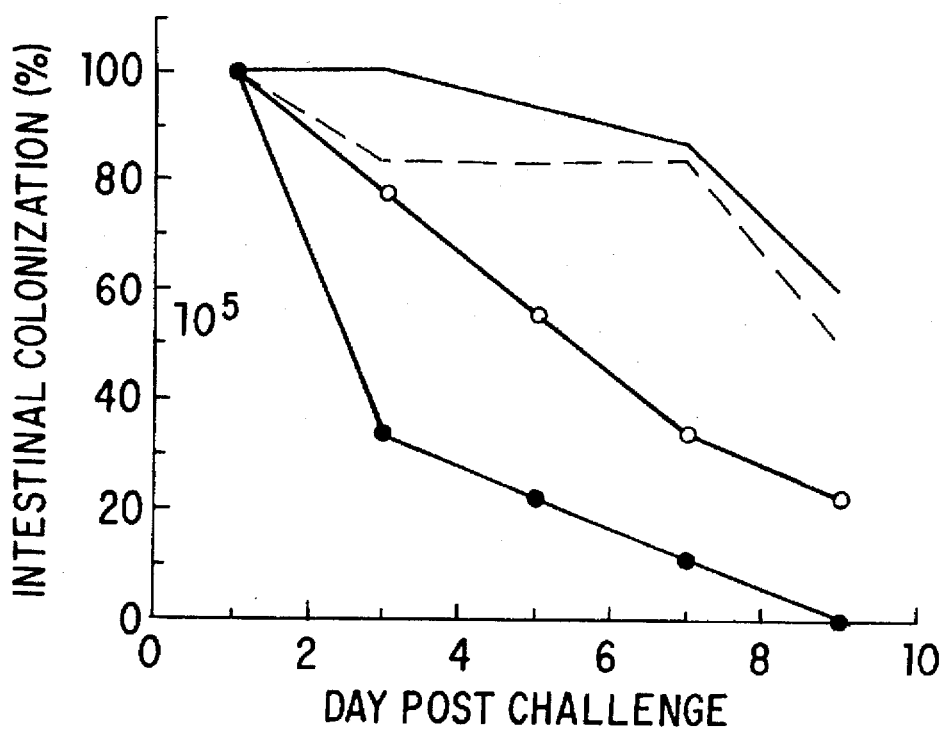
Figure 8B:
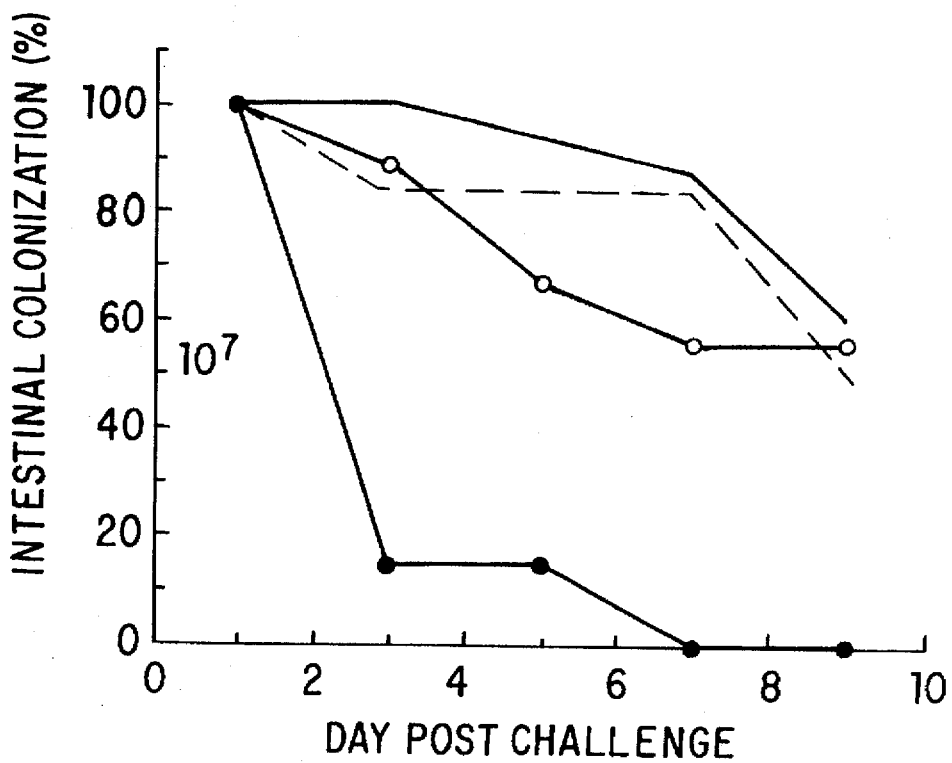
Figure 8C:
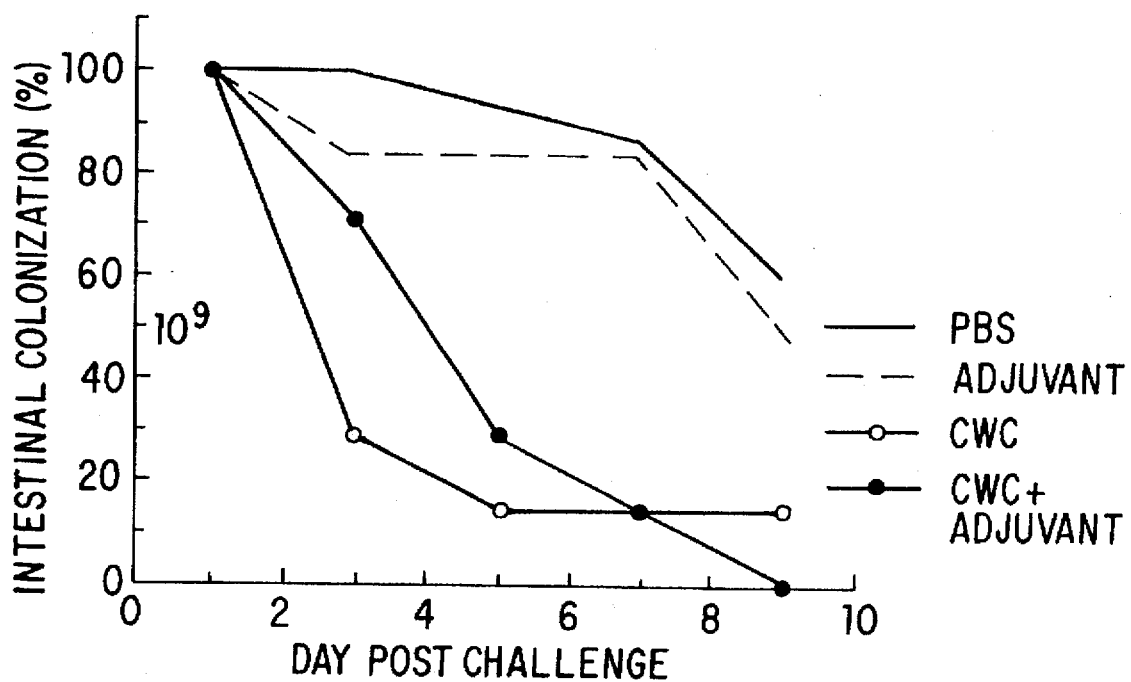

FIGS. 8A, 8B and 8C graphically depict the efficacy of vaccine comprising inactivated *C. jejuni* 81–176 whole cells in protecting mice against an orally delivered challenge of live *C. jejuni* 81–176 cells. Mice were vaccinated as described in the brief description of FIGS. 7A, 7B and 7C. The vaccine efficacy was examined using the intestinal colonization assay. FIG. 8A (top panel) shows the results of the protection afforded by the vaccinations using three oral doses of $10^5$ inactivated bacterial particles per dose. FIG. 8B (middle panel) shows the results of the protection afforded by the vaccinations using three oral doses of $10^7$ inactivated bacterial particles per dose. FIG. 8C (bottom panel) shows the results of the protection afforded by the vaccinations using three oral doses of $10^9$ inactivated bacterial particles per dose. See Example 34 in Section 9 for experimental details.

Figure 9:
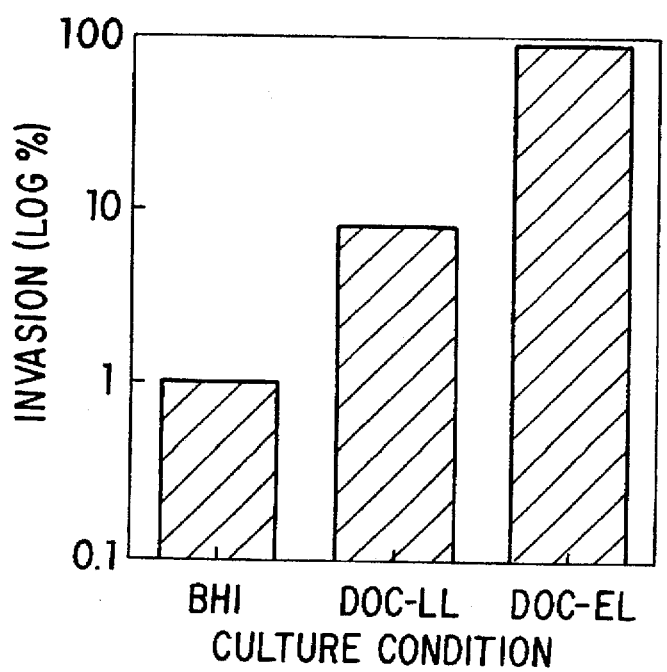

FIG. 9 graphically depicts the effect of the growth phase of the *Shigella flexneri* culture on the invasiveness of the *Shigella flexneri* 2457T cells. *Shigella flexneri* 2457T cells were grown conventionally (BHI), or according to the methods of the present invention as exemplified by Example 9 (DOC-EL)—that is harvesting the cells when the culture is in early log phase—or according to Example 9 but allowing the culture to reach late log phase before harvesting the cells (DOC-LL). The invasiveness of these different preparations of cells are shown. See Example 35 in Section 12 for details.

Figure 10:
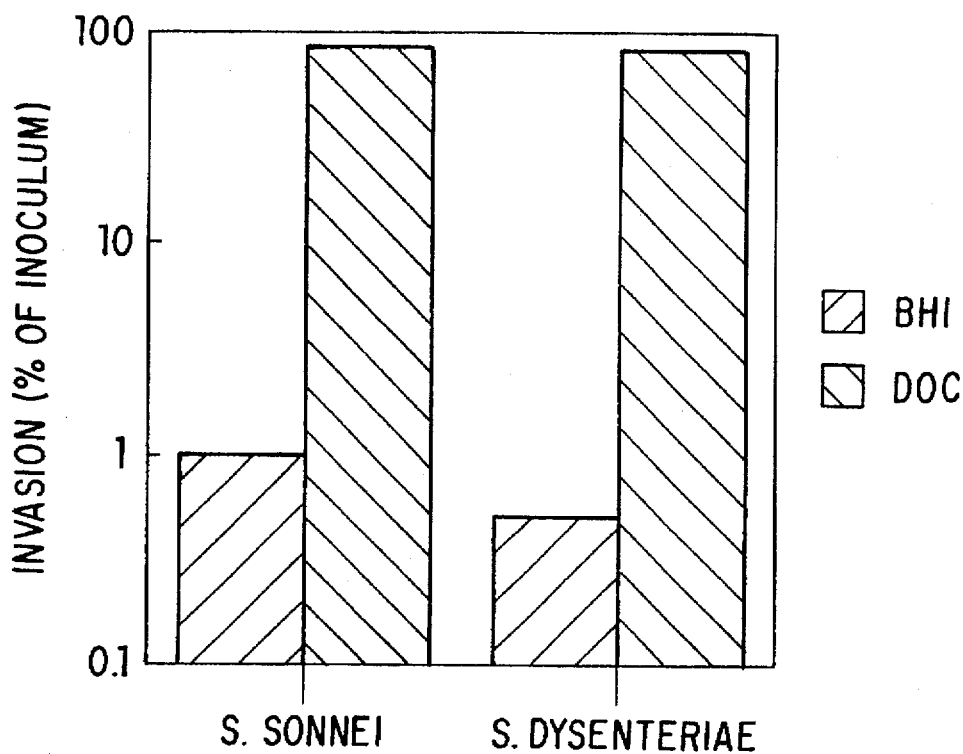

FIG. 10 graphically depicts the enhancement of invasiveness of Shigella cells when they are cultured using the methods of the present invention. *S. sonnei* and *S. dysenteriae* 3818 were cultured conventionally (BHI) or according to the methods of the present invention as exemplified in Example 9. The invasiveness of these different preparations of Shigella cells against INT-407 cells are shown. See Example 35 in Section 12 for details.

Figure 11:
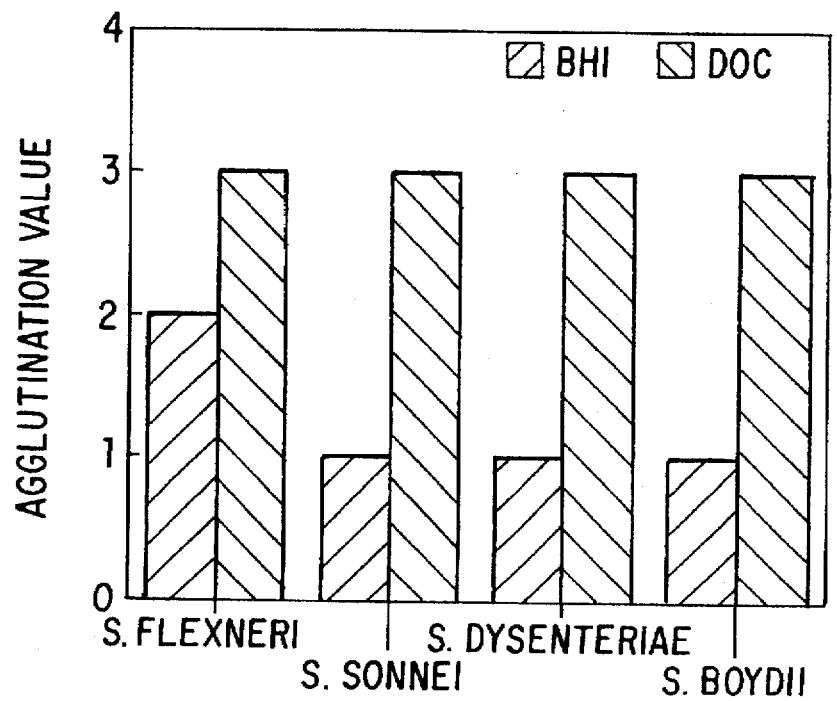

FIG. 11 graphically depicts the enhancement of immunocross reactivity of Shigella grown according to methods of the present invention. *S. flexneri* 2457T grown according to methods of the present invention as exemplified in Example 9 was used to induce antibodies. The agglutination activity of the induced antibodies against *S. flexneri*, *S. sonnei*, *S. dysenteriae* and *S. boydii* grown conventionally (BHI) or according to the methods of the present invention as exemplified in Example 9 serotypes are shown. See Example 36 in Section 12 for details.

Figure 12:
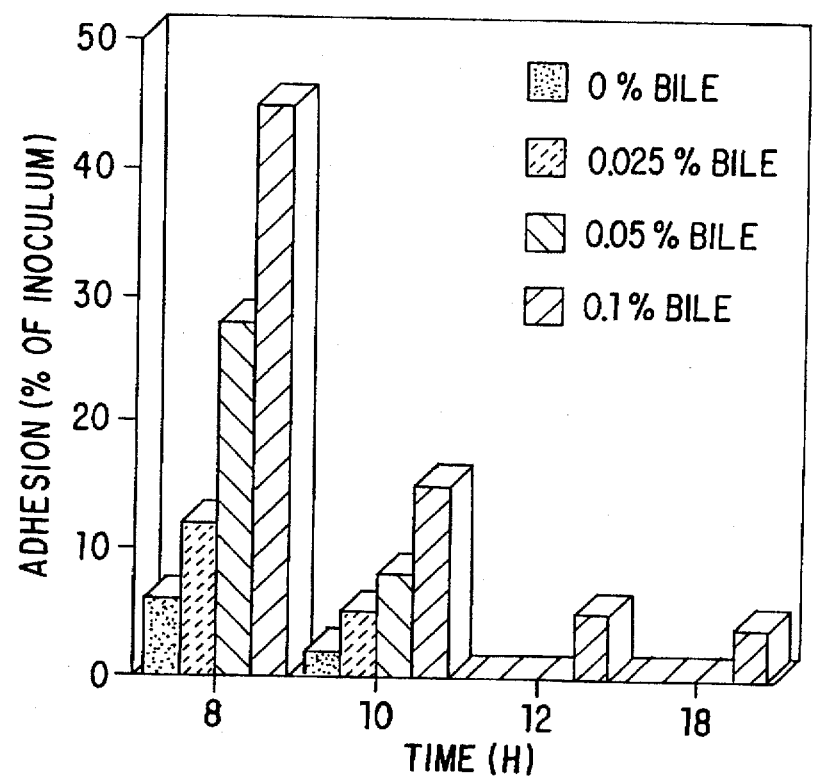

FIG. 12 graphically depicts the effect of bile concentration and the growth phase of the *Helicobacter pylori* culture on the adhesiveness of *Helicobacter pylori* NB3-2 cells. *H. pylori* NB3-2 cells were grown in culture medium containing 0%, 0.025%, 0.05% or 0.1% bile and harvested at 8, 10, 12 and 18 h after inoculation. The invasiveness of these different preparations of *H. pylori* NB3-2 cells against INT-407 cells are shown. See Example 38 in Section 14 for details.

Figure 13:
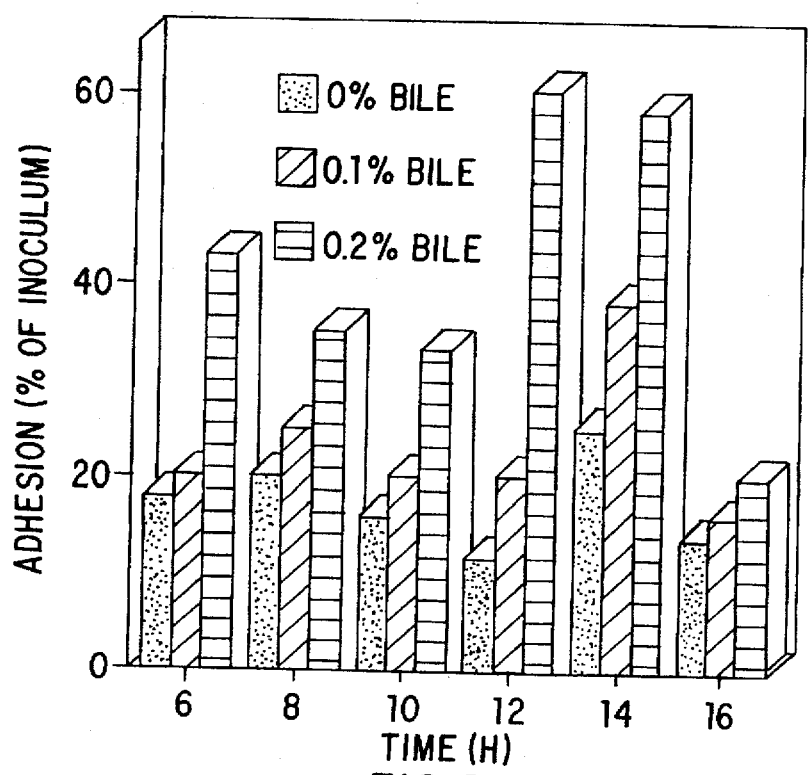

FIG. 13 graphically depicts the effect of bile concentration and the growth phase of the *Helicobacter pylori* culture on the adhesiveness of *Helicobacter pylori* G1–4 cells. *H. pylori* G1–4 cells were grown in culture medium containing 0%, 0.1% or 0.2% bile and harvested at 6, 8, 10, 12, 14 and 16 h after inoculation. The invasiveness of these different preparations of *H. pylori* G1–4 cells against INT-407 cells are shown. See Example 38 in Section 15 for details.

5 DETAILED DESCRIPTION OF THE INVENTION

The methods of the present invention relate to growing enteric bacteria in vitro in the presence of a combination of certain conditions with certain components selected to induce or enhance the expression of antigens and/or virulence factors.

As used herein and in the claims the term "enteric" refers to bacteria normally found in or associated with any part of an animal's gastrointestinal tract and any bacteria that causes an infection in any part of an animal's gastrointestinal tract. Such enteric bacteria include both gram positive and gram negative bacteria.

The terms "components" and "conditions" as used herein and in the claims relate to many factors associated with an enteric bacterium's natural in vivo environment and other factors. Such components and conditions include, but are not limited to, bile, bile acids or salts thereof or their biological precursors such as cholesterol, pH, microaerophillic conditions, osmolarity, and harvesting or collecting the bacteria at a desired bacterial growth phase.

The term "antigens" and its related term "antigenic" as used herein and in the claims includes antigens or antigenic characteristics including, but not limited to, macromolecules contributing to cellular morphology or cell motility; proteins; more particularly surface proteins, lipopolysaccharides and carbohydrates. Preferably said antigens are immunogenic.

The term "immunogenic" as used herein and in the claims refers to the ability to induce antibody production in an animal after said animal is exposed to a composition comprising whole bacteria produced by the present invention or a fragment of said whole bacterium.

The term "antigenically enhanced" or "enhanced antigenic properties" or "enhanced" as used herein and in the claims refers to the antigenic state of enteric bacteria grown according to the methods of the present invention. Such bacteria have higher levels of certain immunogenic antigens and/or new immunogenic antigens as compared to the same bacteria grown using conventional methods.

The term "conventional" as used herein and in the claims relates to what is known in the prior art.

The term "microaerophillic conditions" as used herein and in the claims refers to anaerobic conditions or elevated $CO_2$ levels, such as 5% to 20% $CO_2$ with 80% to 95% air; 5% to 20% $CO_2$ with 80% to 95% $N_2$; or 5% to 10% $O_2$ with 10% to 20% $CO_2$ with 70% to 85% $N_2$.

The term "virulence" as used herein and in the claims refers to those factors of an enteric bacteria associated with the ability to adhere to and/or to invade and/or to survive in a host and/or cause a pathological condition.

The term "immuno-cross protective" as used herein and in the claims refers to the ability of the immune response induced by one bacterial strain or serotype, whole cell or otherwise, to prevent or attenuate infection of the same host by a different bacterial strain, serotype, or species of the same genus.

The term "immuno-cross reactive" as used herein and in the claims refers to the ability of the humoral immune response (i.e., antibodies) induced by one bacterial strain or serotype, whole cell or otherwise, to cross react with (i.e., the antibody binding) a different bacterial strain, serotype, or species of the same genus. Immuno-cross reactivity is indicative of the bacterial immunogen's potential for immuno-cross protection and vice versa.

The term "host" as used herein and in the claims refers to either in vivo in an animal or in vitro in animal cell cultures. The term "animal" as used herein and in the claims includes but is not limited to all warm-blooded creatures such as mammals and birds (e.g., chicken, turkey, ducks etc.)

According to the invention, in a vaccine comprising antigenically enhanced enteric bacteria or an immunogenic fragment or derivative thereof, the enteric bacteria may be either live bacteria or may be inactivated and may further comprise an adjuvant, such as, but not limited to, alum, oilwater emulsion, heat labile toxin from enterotoxigenic *E. coli* (LT) nontoxigenic forms thereof (eg. mLT) and/or individual subunits thereof, Bacille Calmette-Guerin (BCG), or Fruend's adjuvant and may also further comprise a suitable pharmaceutical carrier, including but not limited to saline, dextrose or other aqueous solution. Other suitable pharmaceutical carriers are described in *Remington's Pharmaceutical Sciences*, Mack Publishing Company, a standard reference text in this field. As used herein and in the claims, the term "vaccine" also encompasses "passive vaccines," which comprise antibodies that specifically bind pathogens against whose infections or diseases protection is sought.

The term "inactivated bacteria," as used herein and in the claim, refers to enteric bacteria that are incapable of infection and/or colonization and encompasses attenuated as well as killed bacteria. Attenuated bacteria may replicate but cannot cause infection or disease. Inactivation of said bacteria may be accomplished by any methods known by those skilled in the art. For example, the bacteria may be chemically inactivated, such as by formalin fixation, or physically inactivated such as by heat, sonication or irradiation, so that they are rendered incapable of replication and/or infection and/or causing disease.

An effective amount of the vaccine should be administered, in which "effective amount" is defined as an amount of enteric bacteria or an immunogenic fragment or derivative thereof that is capable of producing an immune response in a subject. The amount needed will vary depending upon the antigenicity of the bacteria, fragment, or derivative used, and the species and weight of the subject to be vaccinated, but may be ascertained using standard techniques. In preferred, non-limiting embodiments of the invention, an effective amount of vaccine produces an elevation of antibacterial antibody titer to at least two times the antibody titer prior to vaccination. In a preferred, specific, non-limiting embodiment of the invention, approximately $10^7$ to $10^{11}$ bacteria and preferably $10^8$ to $10^{10}$ bacteria are administered to a host. Preferred are vaccines comprising inactivated whole bacteria.

The term "effective amount" as applied to passive vaccines is an amount of antibody that is capable of preventing or attenuating a bacterial disease or infection. The amount needed will vary depending upon the type of antibody and the antibody titer, and the species and weight of the subject to be vaccinated, but may be ascertained using standard techniques.

Vaccines of the present invention may be administered locally and/or systemically by any method known in the art, including, but not limited to, intravenous, subcutaneous, intramuscular, intravaginal, intraperitoneal, intranasal, oral or other mucosal routes.

Vaccines may be administered in a suitable, nontoxic pharmaceutical carrier, may be comprised in microcapsules, and/or may be comprised in a sustained release implant.

Vaccines may desirably be administered at several intervals in order to sustain antibody levels.

Vaccines of the invention may be used in conjunction with other bacteriocidal or bacteriostatic methods.

Antibodies of the invention may be obtained by any conventional methods known to those skilled in the art, such as but not limited to the methods described in *Antibodies A Laboratory Manual* (E. Harlow, D. Lane, Cold Spring Harbor Laboratory Press, 1989). In general, an animal (a wide range of vertebrate species can be used, the most common being mice, rats, guinea pig, hamsters and rabbits) is immunized with a whole cell or immunogenic fragment or derivative of an antigenically enhanced enteric bacteria of the present invention in the absence or presence of an adjuvant or any agent that would enhance the immunogen's effectiveness and boosted at regular intervals. The animal serum is assayed for the presence of desired antibody by any convenient method. The serum or blood of said animal can be used as the source of polyclonal antibodies.

For monoclonal antibodies, animals are treated as described above. When an acceptable antibody titre is detected, the animal is euthanized and the spleen is aseptically removed for fusion. The spleen cells are mixed with a specifically selected immortal myeloma cell line, and the mixture is then exposed to an agent, typically polyethylene glycol or the like, which promotes the fusion of cells. Under these circumstances fusion takes place in a random selection and a fused cell mixture together with unfused cells of each type is the resulting product. The myeloma cell lines that are used for fusion are specifically chosen such that, by the use of selection media, such as HAT: hypoxanthine, aminopterin, and thymidine, the only cells to persist in culture from the fusion mixture are those that are hybrids between cells derived from the immunized donor and the myeloma cells. After fusion, the cells are diluted and cultured in the selective media. The culture media is screened for the presence of antibody having desired specificity towards the chosen antigen. Those cultures containing the antibody of choice are cloned by limiting dilution until it can be adduced that the cell culture is single cell in origin. The antibodies of the present invention have use as passive vaccines against enteric bacteria infections and diseases.

Methods for the detection of antibodies or said bacteria in a host include immunoassays. Such immunoassays are known in the art and include, but are not limited to radioimmunoassays (RIA), enzyme-linked immunosorbent assays (ELISA), fluorescent immunoassays, and fluorescence polarization immunoassays (FPIA).

Another embodiment includes diagnostic kits comprising all of the essential reagents required to perform a desired immunoassay according to the present invention. The diagnostic kit may be presented in a commercially packaged form as a combination of one or more containers holding the necessary reagents. Such a kit comprises an enteric bacteria of the present invention, and/or a monoclonal or polyclonal antibody of the present invention in combination with several conventional kit components. Conventional kit components will be readily apparent to those skilled in the art and are disclosed in numerous publications, including *Antibodies A Laboratory Manual* (E. Harlow, D. Lane, Cold Spring Harbor Laboratory Press, 1989). Conventional kit components may include such items as, for example, microtiter plates, buffers to maintain the pH of the assay mixture (such as, but not limited to Tris, HEPES, etc.), conjugated second antibodies, such as peroxidase conjugated anti-mouse IgG (or any anti-IgG to the animal from which the first antibody was derived) and the like, and other standard reagents.

Methods of the present invention include growing enteric bacteria in a suitable basal essential culture medium, such as but not limited to commercially available brain heart infusion broth "BHI", Luria broth "LB", sheep blood agar "SBA", Brucella broth, Meuller-Hinton broth, proteose peptone beef extract broth, etc., with various conditions and components including but not limited to 0.05% to 3% bile or 0.025% to 0.6% of one or more bile acids or salts thereof or biological precursors thereof such as cholesterol, at a temperature between 30° C. and 42° C., until a growth phase at about early log phase, between early log and stationary phases, or at about stationary phase, in air or under microaerophillic conditions, such as 5% to 20% $CO_2$ with 80% to 95% air; 5% to 20% $CO_2$ with 80% to 95% $N_2$; or 5% to 10% $O_2$ with 10% to 20% $CO_2$ with 70% to 85% $N_2$; and optionally in the presence of a divalent cation chelator, such as, but not limited to 0 to 100 µM, preferably 25 µM, of BAPTA/AM 1,2-bis(2-aminophenoxy) ethane-n,n,n',n'-tetraacetic acid/acetoxymethyl ester. Molecular Probes, Eugene, Oreg.), 0 to 10 mM of EGTA (ethylene-bis (oxyethylenenitrilo)-tetraacetic acid; Sigma Chemical Co., St. Louis, Mo.), 0 to 100 µM of EGTA/AM (ethylenebis (oxyethylenenitrilo)-tetraacetic acid/acetoxymethyl ester; Molecular Probes, Eugene, Oreg.); the resulting combination of conditions and components producing antigenically enhanced enteric bacteria.

According to another embodiment, the methods of the present invention also include growing enteric bacteria as described immediately above except in the presence of a divalent cation chelator, such as, but not limited to 1.0 to 100 µM, preferrably 25 µM, of BAPTA/AM, 0.5 to 10 mM of EGTA, or 1.0 to 100 µM of EGTA/AM; but without any bile, bile acids or bile salts.

Bile or bile acids or salts thereof useful for the present invention include any natural bile compound secreted by the liver and normally concentrated in the gall bladder as well as synthetic bile acids known by those skilled in the art, such as but not limited to "OXGALL" (Difco Laboratories, Detroit, Mich.), bovine bile (Sigma Chemicals, St. Louis, Mo.) or other commercially available preparations, cholic, deoxycholic, taurocholic and glycocholic acids. Preferred is deoxycholate (DOC), a commercially available bile acid present in vivo in the distal small intestine and large intestine sites colonized by some enteric bacteria. Also preferred is glycocholate (GC).

According to the present invention, enteric bacterial cultures selected from the group of Campylobacter spp., Helicobacter spp., Gastrospirillum spp., Bacteroides spp., Klebsiella spp., Enterobacter spp., Salmonella spp., Shigella spp., Aeromonas spp., Vibrio spp., Clostridium spp., Enterococcus spp. and *Escherichia coli* can be prepared as frozen stocks by methods generally known to those skilled in the art and maintained at −80° C. for future use. For instance, stocks of *Campylobacter jejuni* can be prepared by growing the organism on trypticase soy agar containing 5% defribinated sheep erythrocytes (SBA), at 37° C. in 5% $O_2$, 10% $CO_2$, 85% $N_2$ (microaerophilic condition, "MC") for 20 h. Stocks of *Escherichia coli, Salmonella typhimurium, Helicobacter pylori* and *Shigella flexneri* can be prepared by growing the organism in brain heart infusion broth ("BHI"). Bacteria can be harvested for freezing by any known method, for instance by swabbing the culture and resuspending in BHI containing 30% glycerol. Cultures for analytical experiments or for production fermentations can be prepared by any generally known methods, such as by growing the organism on BHI with 1.5% agar at 37° C. under MC or atmospheric conditions and then transferring a single colony to broth and culturing according to methods of the present invention described herein. Bacteria can be harvested for use by any method generally known to those skilled in the art, such as by centrifugation.

In preferred embodiments, antigenically enhanced cells of Campylobacter sp., preferably of the species *jejuni* or *coli* and most preferably of the *jejuni* strain 81–176, are grown in a basal essential culture medium, preferably BHI broth, additionally comprising about 0.1% DOC or about 0.8% bile at 37° C. in a mixture of about 10 to 20% $CO_2$ with about 80 to 90% air and harvested after the growth of the culture has reached about late log phase to about stationary phase, typically about 20 h after inoculation.

In other preferred embodiments, antigenically enhanced cells of Shigella sp., preferably of the species *flexneri* or *dysentariae* and most preferably of the *flexneri* strain 2457T, are grown in a basal essential culture medium, preferably BHI broth, additionally comprising about 0.1% DOC or about 0.8% bile at 37° C. in air and harvested after the growth of the culture has reached about early log phase, typically about 30 min after inoculation with a culture that is at early to mid log phase.

In further preferred embodiments, antigenically enhanced cells of *Helicobacter pylori*, preferably of the strain ATCC 49503, NB3-2 or G1-4, are grown in a basal essential culture medium, preferably BHI broth, additionally comprising about 0.05% to about 0.2% bile or about 0.05% glycocholate (GC) at 37° C. in a mixture of about 5% to 20% $CO_2$ with about 80% to 95% air, or about 10% $CO_2$ with about 5% $O_2$ with about 85% $N_2$ and harvested after the growth of the culture has reached about log or about stationary phase. In a more preferred embodiment, the cells are harvested after the culture has reached about log phase.

Enteric bacteria cultured according to the methods of the present invention have altered morphologies, and/or cell motilities and/or produce certain new proteins, lipopolysaccharides and/or carbohydrates and/or such macromolecules at altered levels compared to cells cultured in basal medium alone. Optimum cultural conditions that enhance cell yield and the indices of pathogenicity can be identified. Utilizing these cultural conditions, virulence-associated antigens that are enhanced or induced can be identified.

Motility and gross morphological changes can be seen by microscopic examination of either untreated or stained bacteria. It is possible that other morphological changes might result from methods of the present invention as could be seen through electron microscopy or fluorescence microscopy.

The morphology and mucus-like characteristics of the enteric bacteria cultured according to methods of the present invention suggest that capsule and/or surface layer expression might be induced. To test for capsule production, phenol extracts of surface components, such as proteins, carbohydrates and lipopolysaccharides, can be prepared. The enhanced carbohydrates can be seen by high pressure liquid chromatography (HPLC).

Protein profiles of outer membranes prepared from enteric bacteria grown under virulence enhancing growth condictions of the present invention can be characterized by sodium dodecyl sulfate-polyacrylamide gel electrophoresis (SDS-PAGE) and compared to those from organisms grown in conventional media. SDS-PAGE is conducted to evaluate changes induced in bacterial cellular and extracted proteins in response to antigen enhancing or altering conditions. These data offer qualitative and quantitative information concerning surface changes associated with increased invasiveness or altered antigenicity.

The immunogenic potential of induced or altered protein antigens can be identified by Western Blotting. Immunogenicity of induced or altered bacterial proteins identified by SDS-PAGE can be evaluated by the generally accepted techniques of Western Blotting as described below. Any source of antibody can be used, such as convalescent immune rabbit or ferret sera (source of antibody from animals infected orally with live organisms grown conventionally or according to methods of the present invention), intestinal mucus (source of IgA antibody), polyclonal antisera, or a monoclonal antibody, for instance one that is cross-reactive with *C. jejuni* flagellin, for assaying bacterial antigens.

The increased production of several of these bacterial antigens is accompanied with enhancement of properties associated with virulence. These properties include adhesion to and invasion of cultured human intestinal epithelial cells, and Congo red dye binding. The Congo red dye binding assay is a generally accepted method predictive of virulence and is described below and in Andrews et al., (*Infect. Immun.*, 60:3287–3295, 1992); and Yoder (*Avian Dis.*, 33:502–505, 1989). Bacterial binding of Congo red indicates ability to bind hemin, this ability to bind hemin is correlated with virulence. Congo red binding also correlates with enhanced bacterial invasion of epithelial cells.

Previously it has been shown that most conventionally grown *C. jejuni* Lior serotypes are not immuno-cross reactive. Based on this information, it would be necessary to prepare and administer a number of vaccines of several Lior serotype strains or a combination vaccine to obtain generalized protection against Campylobacter. Antigenically enhanced Campylobacter produced according to methods of the present invention are immuno-cross reactive against a broader range of Lior serotypes than that obtained using conventionally grown Campylobacter. Similarly, antigenically enhanced Shigella produced according to the methods of the present invention are immuno-cross reactive and immuno-cross protective against a broader range of Shigella species than that obtained using conventionally grown Shigella. These immuno-cross reactive and immuno-cross protective properties are indicated by the results of agglutination assays and vaccine studies described below.

Methods of the present invention for production of antigenically enhanced enteric bacteria correlate to enhanced virulence in small animal models. Several domestic animals can be used as models of Campylobacter disease in humans. The most studied from the standpoint of immunization efficacy is the reversible intestinal tie, adult rabbit diarrhea (RITARD Model) of Caldwell, et al., (*Infect. Immun.*, 42:1176–1182, 1983). This model has also demonstrated the association of Lior serotypes with cross-strain protection. However, this model measures resistance to colonization rather than resistance to disease. The ferret model of Bell et al. (*Infect. Immun.*, 58:1848–1852, 1990) may be a more useful model because this animal does develop disease symptoms like those of Campylobacter disease in humans. A more recent model is the mouse colonization model of Bagar (*Infection and Immunity*, 63:3731–3735, 1995). This model involves immunization followed by nasal or oral challenges with live Campylobacter to the immunized mouse and then examination of intestinal colonization by monitoring for the presence of Campylobacter in fecal matter. With Shigella, the mouse nasal challenge assay as described by Mallett et al. (see infra Section 13) is used to assess virulence and vaccine efficacy. With *Helicobacter pylori*, the *Helicobacter felis* gastric colonization model described by Chen et al. (*Lancet*, 339:1120–1121, 1992) is used to evaluate the vaccine potential of *H. pylori* produced by the methods of the present invention.

There are other animal models relevant to enteric bacterial invasion and infection and they can be used to test for vaccine efficacy of the enhanced enteric bacteria produced according to the methods of the present invention.

The antigenically enhanced enteric bacteria produced by the methods of the present invention are used to prepare prototype killed whole-cell or subunit vaccines. These vaccines when administered to animals can be shown to induce antibodies and thus establish the vaccines' protective potential. Elevation or induction of these antigens in a bacterial cell produces cells that make more efficacious vaccines.

Vaccine candidate preparations produced by the methods of the present invention can be used with various mucosal immunization strategies to induce an intestinal immune response. Successful immunization protocols can then be used to protect animals challenged with the pathogens with or without enhanced antigenicities. Also vaccines can be formulated and tested as combined vaccines, for example Shigella and Campylobacter cells or components thereof can be combined as a single vaccine.

The experimental approaches described below enable the detection of changes in surface antigens and other characteristics which are associated with enhanced invasiveness. These changes are both qualitative and quantitative. Most importantly, these experiments establish that the methods of the present invention enhance invasiveness and induce immunogenically relevant antigens. Such antigenically enhanced bacteria induce an immunogenic response which is protective against infections by a broader range of bacterial strains, serotypes and/or species and are therefore useful as efficacious vaccines as compared to conventionally grown bacteria.

Several well-established models generally known to those skilled in the art exist and are useful to evaluate enhanced antigenic properties, virulence of bacteria and vaccine efficacy as described below.

Non-limiting examples of the present invention are described below.

EXAMPLES

METHODS FOR PRODUCING ENHANCED ANTIGENIC BACTERIA

Example 1

*Campylobacter jejuni* strain 81–176 was streaked on blood agar plates (containing trypticase soy agar, plus 5% defibrinated sheep erythrocytes) and incubated in a microaerophilic GasPak jar (BBL, Cockeysville, Md.) for 20 h at 37° C. Lawns of bacteria were removed by swabbing and inoculated into flasks containing 1 liter of BHI medium pre-equilibrated to 10% $CO_2$, 90% air, with 0.8% OXGALL (Difco, Detroit, Mich.). Cultures were incubated for 20 h with shaking at 37° C. in a closed flask at 10% $CO_2$, 90% air and then harvested as described above.

Example 2

*Campylobacter jejuni* strain 81–176 was streaked on blood agar plates (containing trypticase soy agar, plus 5% defibrinated sheep erythrocytes) and incubated in a microaerophilic GasPak jar (BBL, Cockeysville, Md.) for 20 h at 37° C. Lawns of bacteria were removed by swabbing and inoculated into flasks containing 1 liter of BHI medium pre-equilibrated to 10% $CO_2$ with 0.01% to 0.1% sodium deoxycholate (DOC). (It is critical to prepare and autoclave the DOC as a stock solution separate from the BHI medium, and to aseptically add it to the BHI medium to a final concentration of 0.01% to 0.1% immediately before inoculation of the bacteria). Cultures were incubated for various times up to 20 h with shaking at 37° C. in 5% $O_2$, 10% $CO_2$, 85% $N_2$, then harvested as described above.

Example 3

*Campylobacter jejuni* strain 81–176 was streaked on blood agar plates (containing trypticase soy agar, plus 5% defibrinated sheep erythrocytes) and incubated in a microaerophilic GasPak jar (BBL, Cockeysville, Md.) for 20 h at 37° C. Lawns of bacteria were removed by swabbing and inoculated into flasks containing 1 liter of Brucella broth pre-equilibrated to 10% $CO_2$ with 0.01% to 0.1% sodium deoxycholate. Cultures were incubated for 20 h with shaking at 37° C. in 5% $O_2$, 10% $CO_2$, 85% $N_2$ and then harvested as described above.

Example 4

*Campylobacter jejuni* strain 81–176 was streaked on blood agar plates (containing trypticase soy agar, plus 5% defibrinated sheep erythrocytes) and incubated in a microaerophilic GasPak jar (BBL, Cockeysville, Md.) for 20 h at 37° C. Lawns of bacteria were removed by swabbing and inoculated into flasks containing 1 liter of Mueller-Hinton broth pre-equilibrated to 10% $CO_2$, with 0.01% to 0.1% sodium deoxycholate. Cultures were incubated for 20 h with shaking at 37° C. in 5% $O_2$, 10% $CO_2$, 85% $N_2$ and then harvested as described above.

Example 5

*Campylobacter jejuni* strain 81–176 was streaked on blood agar plates (containing trypticase soy agar, plus 5% defibrinated sheep erythrocytes) and incubated in a microaerophilic GasPak jar (BBL, Cockeysville, Md.) for 20 h at 37° C. Lawns of bacteria were removed by swabbing and inoculated into flasks containing 1 liter of BHI medium pre-equilibrated to 10% $CO_2$, with 0.1% sodium deoxycholate. Cultures were incubated for 20 h with slow stirring at 37° C. in 10% $CO_2$, 90% air and then harvested as described above.

Example 6

*Vibrio cholerae* is streaked on BHI agar plates (containing trypticase soy agar, plus 5% defibrinated sheep erythrocytes) and incubated in air for 20 h at 37° C. Lawns of bacteria are removed by swabbing and inoculated into flasks containing 1 liter of BHI medium with 0.1% sodium deoxycholate. Cultures are incubated for 20 h with shaking at 37° C. in air, then harvested as described above.

Example 7

*Salmonella cholerasius* is streaked on BHI agar plates and incubated in air for 20 h at 37° C. Lawns of bacteria are removed by swabbing and inoculated into flasks containing 1 liter of BHI medium with 0.1% sodium deoxycholate. Cultures are incubated for 20 h with shaking at 37° C. in air, then harvested as described above.

Example 8

*Salmonella typhimurium* is streaked on Luria broth agar plates and incubated for 20 h at 37° C. in air. Lawns of bacteria are inoculated into flasks containing 1 liter of BHI medium with 0.1% sodium deoxycholate. Cultures are incubated for 20 h with shaking at 37° C. in 10% $CO_2$, 90% air. One colony is transferred into 1 liter of LB containing 0.1% DOC and incubated in a closed top flask at 37° C. with slow shaking. After 12 h, 60 ml of the culture is diluted into 1 liter of the same fresh prewarmed medium and incubated a further 30 min, and then is harvested as described above.

Example 9

*Shigella flexneri* 2457T was streaked on Congo red agar plates and incubated for 20 h at 37° C. in air. One red colony was inoculated into flasks containing 1 liter of BHI media and incubated with shaking for 12 h. 50 ml of this culture was then used to inoculate 250 ml of prewarmed BHI containing 0.1% sodium deoxycholate. The culture was incubated with shaking for 4 h at 37° C. in air. This culture was then diluted to an $OD_{600}$ of about 0.17 with prewarmed BHI containing 0.1% DOC and incubated for 30 min with shaking at 37° C. in air, and then harvested as described above.

Example 10

*Campylobacter jejuni* 81-176, 81-116, or HC (in BHI with 30% glycerol) was rapidly thawed and plated on sheep blood agar (SBA, 0.1 ml per plate). The inoculated plates were incubated in a GasPak jar with a CampyPak Plus microaerophilic environment generator (BBL, Cockeysville, Md.) for 20 h at 37° C. The bacterial lawn was removed from the plates by swabbing, and the bacteria were resuspended in 10 ml of BHI. The bacterial suspension was inoculated into 1 liter of BHI broth alone or BHI broth containing 0.1% DOC, pre-equilibrated to 10% $CO_2$, 90% air, in a 2 liter flask. The inoculum was added to preequilibrated medium until the $OD_{625}$ is equal to 0.05. The inoculated flask was returned to the 10% $CO_2$ with 90% air and stirred slowly for 20 h at 37° C. At this point the bacteria were harvested as described above.

Example 11

*Helicobacter pylori* was added to BHI broth plus 4% bovine calf serum. After inoculation the flasks were flushed with 5% $O_2$, 10% $CO_2$, 85% $N_2$ and incubated for 22 h at 37° C. with shaking. After this incubation, 2.5 ml of the culture was transferred to a flask containing BHI broth with 4% bovine calf serum or the same medium additionally containing 0.05% sodium glycocholate. These cultures were again flushed with the microaerophilic gas mixture (5% $O_2$, 10% $CO_2$ 85% $N_2$), and incubated 20-24 h at 37° C. The cells were harvested as described above.

Example 12

*Salmonella typhimurium* (in LB with 30% glycerol) was streaked on a LB agar plate and cultured for 18-20 h at 37° C. in air. One colony was picked and transferred into 1 liter of LB or LB containing 0.1% DOC in flasks that are flushed with 10% $CO_2$, 5% $CO_2$, 85% $N_2$, sealed and incubated for 12 h at 37° C. with shaking. The bacteria were then diluted in the same media to $OD_{600}$ of 0.17 and incubated under identical conditions until the culture reaches early log phase, typically 30 min after the dilution. Cells were harvested as described above.

Example 13

*Salmonella typhimurium* is streaked on a LB agar plate and cultured for 18-20 h at 37° C. in air. One colony is picked and transferred into 1 liter of LB or LB containing 0.1% DOC and incubated for 12 h at 37° C. in air. The culture is then diluted (⅕) in the same fresh media and incubated a further 4 hours under identical conditions. The cultures are then diluted in the same fresh media to $OD_{600}$ of 0.17 and incubated under identical conditions until the culture reaches log phase, typically 30 minutes after the dilution. Cells are harvested as described above.

Example 14

*Klebsiella pneumoniae* is streaked on a BHI agar plate and incubated 18-20 h at 37° C. in air. One colony is picked and inoculated into 1 liter of BHI or BHI containing 0.1% DOC and shaken for 12 h at 37° C. in air. The bacteria are then diluted in the same media to $OD_{600}$ of 0.17 and grown for 30 min further and then harvested as described above.

Example 15

*Enterobacter cloacae* is streaked on a BHI agar plate and incubated at 37° C. in air for 18-20 h. One colony is inoculated into 1 liter of BHI or BHI containing 0.1% DOC and shaken for 12 h at 37° C. The bacteria are then diluted in the same media to $OD_{600}$ of 0.17 and grown for 30 min further and then harvested as described above.

Example 16

*Escherichia coli* strain 0157:H7 was streaked on sheep blood agar plate and incubated at 37° C. in air for 18-20 h. One colony was inoculated into 1 liter BHI or BHI containing 0.1% to 0.2% DOC flask and shaken for 12 h at 37° C.

The bacteria were then diluted to $OD_{600}$ of 0.17 and grown for 30 min further and then harvested as described above.

Example 17

*Enterococcus faecalis* is streaked on sheep blood agar plate and incubated at 37° C. in air for 18-20 h. One colony is inoculated into 1 liter BHI or BHI containing 0.1% DOC flask and shaken for 12 h at 37° C. The bacteria are then diluted to $OD_{600}$ of 0.17 and grown for 30 min further and then harvested as described above.

Example 18

*Clostridium difficile* (modified chopped meat medium with 30% glycerol) is streaked on a plate of Beef liver medium for anaerobes containing 1.5% agar and cultured at 37° C. under microaerophillic conditions (5% $CO_2$ and 95% $N_2$). One colony is transferred to 1 liter of modified chopped meat medium or same medium containing 0.1% DOC. The bacteria are cultured under microaerophillic conditions at 37° C. for 12 h, and harvested as described above.

Example 19

*Bacteroides fragilis* (modified chopped meat medium with 30% glycerol) is streaked on a modified chopped meat medium agar plate and cultured at 37° C. under microaerophillic conditions (5% $CO_2$ and 95% $N_2$). One colony is transferred to 1 liter of modified chopped meat medium or same medium containing 0.1% DOC. The bacteria are cultured under microaerophillic conditions at 37° C. for 12 h, and harvested as described above.

Example 20

*Yersinia pseudotuberculosis* (Luria broth containing 30% glycerol) is streaked on a Luria broth agar plate and incubated at 30° C. One colony is transferred to 1 liter of LB and incubated for 12 h at 30° C. This culture is diluted (⅕) in LB or LB containing 0.1% DOC and incubated 4 h at 37° C. Subsequently, the cultures are diluted in the same media to $OD_{600}$ of 0.17 and incubated a further 30 min and then harvested as described above.

Example 21

*Helicobacter pylori* was added to BHI broth plus 4% bovine calf serum. After inoculation the flasks were flushed with 5% $O_2$, 10% $CO_2$, 85% $N_2$ and incubated for 22 h at 37°

C. with shaking. After this incubation, 2.5 ml of the culture was transferred to a flask containing BHI broth with 4% bovine calf serum or the same medium additionally containing about 0.1% to about 0.2% bovine bile. These cultures were again flushed with the microaerophilic gas mixture (5% $O_2$, 10% $CO_2$ 85% $N_2$), and incubated 20–24 h at 37° C. The cells were harvested as described above.

7 EXAMPLES: ENHANCED ANTIGENIC BACTERIA

Example 22

Microscopic examination of wet mounted bacteria was utilized to observe motility and gross morphology. Surface layers were observed by capsule staining in india ink (nigrosine). After air drying, the cells were counter-stained with crystal violet. All observations were at 1000× magnification.

Morphology of bacteria cultured according to methods of the present invention (hereinafter referred to as "ENHANCED" bacteria) was altered compared to those cultured in basal media alone (conventionally grown). For instance, "ENHANCED" C. jejuni aggregated, and formed large clumps of cells, while conventionally grown cells were predominantly solitary. It was apparent from capsule staining (data not shown) that a change in the bacterial surface was effected by culturing using methods of the present invention. This surface alteration actually resulted in the increased binding by "ENHANCED" cells of the nigrosine particles from the stain. The "ENHANCED" bacteria remained highly motile.

Example 23

C. jejuni surface components were analyzed by phenol extraction. Extracts were made from C. jejuni 81–176 grown conventionally or cultured according to Example 2 above. C. jejuni cells were harvested from culture medium by centrifugation as described above. The cell pellet was extracted for 2 h at room temperature with 1% phenol. Intact cells were separated from extracted materials by centrifugation for 45 min. The supernatant containing extracted bacterial surface components was dialyzed against distilled water overnight. The retentate was centrifuged 105,000× g for 3 h at 4° C. The extract pellet was redissolved in 10% NaCl and precipitated with two volumes of cold 95% ethanol. The precipitation was repeated, and the sample was lyophilized. Subsequently, the sample was dissolved in water at 1 mg/ml for further analysis.

Carbohydrate content of the extract was assayed with the generally accepted phenol-sulfuric acid method utilizing glucose as a standard. Uronic acid content of the extract was measured with the method of Dische using the carbazole reagent. Total protein content of the phenol extract was evaluated with the biccichinoic acid assay kit (Pierce Chem. Co., Rockford, Ill.).

It was notable that uronic acid was absent from the extracts. Many typical bacterial capsules are composed of uronic acid polymers. Surprisingly, surface extracts of C. jejuni 81–176 were in fact predominantly protein. However, total carbohydrate content of the "ENHANCED" cell extracts was increased over cells grown conventionally.

The carbohydrate to protein ratio of the extracts is shown in Table 1 below.

TABLE 1

Carbohydrate:Protein Ratio of Cell Surface Extracts of C. jejuni Grown Conventionally (BHI) or According to Method of Example 2 (ENHANCED)

| Time after addition (h) | BHI | ENHANCED |
| --- | --- | --- |
| 1 | 0.02 | 0.02 |
| 2 | 0.02 | 0.10 |
| 4 | 0.02 | 0.15 |
| 6 | 0.03 | 0.29 |

There was a direct relationship between inclusion of DOC in the culture medium and enhanced levels of surface extractable carbohydrate from the bacterium (Table 1). Surface extractable carbohydrates were increased more than 8-fold in bacteria cultured according to the methods of the present invention; no increase was seen in bacteria grown conventionally. The aggregation of the bacterial cells cultured in DOC medium appeared to be attributable to the components of the surface extract.

Upon rehydration, the extract had a high gelling capacity in water rendering the solution highly viscous and mucus-like, which was similar in character to the aggregated bacteria. The functionality of the extract resembled mucin-like glycoproteins.

For analysis of individual monosaccharides, extracts were hydrolyzed in 1N trifluoroacetic acid in sealed vials. The samples were dried under nitrogen 2 h, and resuspended in distilled water. Sugars were separated by HPLC using a Dionex Corp chromatographic matrix and a solvent system consisting of 3% of 0.5N NaOH/97% $H_2O$ as solvent. Amperometric detection was utilized for measurement of separated monosaccharides. An authentic monosaccharide standard composed of fucose, galactosamine, glucosamine, galactose, glucose, and mannose was also subjected to HPLC analysis for comparison.

HPLC analysis of the hydrolyzed surface extract revealed the presence of several monosaccharides (FIG. 1). There appeared to be no qualitative difference in the carbohydrate composition of the extracts from conventionally grown or bacteria grown according to the method of Example 2 above. However, minor quantitative differences were apparent.

Example 24

Bacterial proteins were analyzed by SDS-PAGE and Western Blotting. The gel system of Lugtenberg, et al. (FEBS Letters 58:254–258, 1975) was used. The gel system is a discontinuous gel consisting of a low acrylamide (typically 4%) stacking gel pH 6.8, and a higher percentage acrylamide separation gel pH 8.8. SDS (0.1%) was included in both gels and all buffers used. Protein separation was according to molecular size, and 8 or 12% acrylamide separation gels were used. Visualization of separated proteins was by silver staining of fixed gels, and molecular size determinations were made based on the $M_r$ values of known proteins used as standards.

C. jejuni cell proteins were separated by SDS-PAGE and visualized by silver staining. Four proteins including a 62 kDa protein were induced or enhanced in cells cultured with DOC (FIG. 2).

Example 25

S. flexneri LPS was analyzed by phenol extraction. S. flexneri cells grown conventionally or according to the present invention as exemplified in Example 9 above were harvested from culture medium by centrifugation as described above. Lipopolysaccharides (LPS) were extracted by the method of Westphal and Jann (In: R. Whistler, ed., *Methods in Carbohydrate Chemistry*, vol 5; p. 83, 1965). Briefly, cells cultured in BHI or as exemplified in Example 9 above were harvested by centrifugation and washed once in PBS. The cells were then extracted for 15 min at 68° C. with 45% phenol in water. The extract was cooled to 10° C. and centrifuged. The LPS-containing upper aqueous phase was aspirated off and dialyzed against distilled water. The retentate was centrifuged 7 h at 80,000× g, 4° C. once, and three times for 3 h each at 105,000× g. The final pellet was lyophilized. Prior to analysis the LPS was resuspended in water (1 mg/ml). The purified LPS was characterized as to carbohydrate content as described above, and by sodium dodecyl sulfate-polyacrylamide gel electrophoresis (SDS-PAGE) as described below and shown in FIG. 5.

*S. flexneri* protein profiles revealed no major differences between conventionally cultured and "ENHANCED" cells when analyzed using this particular SDS-PAGE system. Carbohydrate to dry weight ratios of LPS from "ENHANCED" cells was decreased as compared to extracts from BHI cells. However, SDS-PAGE followed by oxidation and silver staining of *S. flexneri* LPS demonstrated a major change in LPS structure (FIG. 5). As seen in lane "2" of the gel, the O-antigen fraction of LPS from "ENHANCED" *S. flexneri* was reduced in length. This result complemented the findings of reduced carbohydrate/dry weight ratio of LPS from "ENHANCED" cells.

These results suggest shorter O-antigen side chain presentation on "ENHANCED" cells, and potentially might render the bacteria more hydrophobic. A more hydrophobic bacterium might have greater interaction with hydrophobic surfaces in the gut.

Example 26

Immunogenicity of proteins was determined by Western Blots. Proteins from bacteria grown conventionally or according to the methods of the present invention as exemplified in Example 1 or 5 above were separated by SDS-PAGE, then were electrophoretically transferred to nitrocellulose or PVDF membranes and were blocked with a standard blocking agent [3% BSA, 50 mM Tris (pH 8.5), 50 mM NaCl, 0.2% TWEEN 20]. Primary antibody was applied in blocking buffer, the blot was then washed and a secondary antibody reporter cognate was applied. Following washing, the blot was visualized with light or chromophore producing substrates. The reporter moiety used was horse radish peroxidase or alkaline phosphatase.

FIG. 3 depicts proteins from Western Blotting with immune rabbit mucus containing IgA. As can be seen, the 62 kDa protein was the immunodominant antigen. The antigenicity of the 62 kDa protein was greatly enhanced in cells cultured with DOC or bile. This protein was also the predominant antigen in the surface extract of cells cultured with DOC.

Utilizing a mouse monoclonal antibody cross-reactive with *Campylobacter flagellin*, it was demonstrated that the enhanced protein was *C. jejuni* flagellin (FIG. 4). This was a significant finding because several researchers have demonstrated that the *C. jejuni* flagellin is involved in pathogenesis and associated with the invasive characteristics of the bacterium.

Example 27

Congo red dye binding was used to measure virulence. Enteric bacteria grown conventionally (BHI) or according to the methods of the present invention ("ENHANCED") on BHI agar plates and containing 0.025% Congo red were resuspended in distilled water and extracted with acetone for 10 min. Cellular debris was pelleted by centrifugation, and the $OD_{488}$ of the dye was measured with a blank solution of 40% acetone, 60% water. The dye absorbance was compared to the cell absorbance at 660 nm and expressed as the ratio of $OD_{488}/OD_{660}$. The data are shown in Table 2 below.

TABLE 2

Congo Red Dye Binding of Enteric Pathogenic Bacteria Grown Conventionally (BHI) or According to Methods of the Present Invention (ENHANCED)

| Strain | Dye Absorbance | |
|---|---|---|
|  | BHI | ENHANCED |
| *C. jejuni* 81-176 | 0.07 | 0.49 |
| *C. jejuni* 81-116 | 0.06 | 0.49 |
| *S. typhimurium* SR11 | 0.05 | 0.30 |
| *S. flexneri* 2457T | 0.02 | 0.13 |
| *V. cholera* 569b | 0.70 | 2.00 |

Table 2 shows that for several species of enteric bacteria cultured according to methods of the present invention, Congo red dye binding was enhanced. These results show that in vitro methods of the present invention are useful to induce virulence and other characteristics known to correlate with in vivo pathogenesis for other bacterial species.

Example 28

Bacterial adhesion to cultured epithelial cells was analyzed. Bacterial adhesion was assayed as described by Galan and Curtiss (*Proc. Natl. Acad. Sci. USA*, 86:6383–6387, 1989). Tissue culture cells (INT-407 or Henle cells (ATCC #CCL6), and CaCo-2 (ATCC #HTB37) human intestinal cell lines) were cultured in 24-well tissue culture plates (37° C., 5% $CO_2$) to a confluency of 60–80%. The medium is dependent on the cell line used, but Dulbecco's modified Eagle's medium with 10% fetal bovine serum and 50 mg/ml each of penicillin G and streptomycin was used for Henle cells, and RPMI 1640 medium with 10% fetal bovine serum and 50 mg/µl each of penicillin G and streptomycin was used for the culture of CaCo-2 cells. At least 3 h before assay, the culture medium was removed and the cells were washed twice with Hank's balanced salt solution (HBSS) with magnesium and calcium. The monolayers were then overlayed with antibiotic-free growth medium.

For adhesion assays, the bacteria were prepared as follows. For slow growing enteric bacteria such as Campylobacter and Helicobacter the bacterial culture density was diluted to an $OD_{625}$ of 0.1 with fresh, preequilibrated medium and then used in the assay. For Shigella and other fast growing enteric bacteria, the bacterial culture was diluted to 0.17 at $OD_{625}$ with fresh, preequilibrated medium and then used in the assay. The bacteria were added to the epithelial cells at a multiplicity of infection of 10 bacteria per cell to avoid saturation. The number of bacteria inoculated into the tissue culture well was calculated by plate counting. Following 2 h infection under 5% $CO_2$ for Campylobacter, and 30 min for Shigella, unbound bacteria were removed by washing with HBSS before lysis of the monolayer with 0.1% deoxycholate and plating for the determination of adhesion.

The effect of temperature on adhesion to INT-407 cells by *C. jejuni* 81–176 grown conventionally or according to the methods of the present invention as exemplified in Example 5 above is shown in Table 3 below.

Differences in adhesion of several strains of *C. jejuni* grown conventionally or according to methods of the present invention are shown in Table 4 below.

Percent adhesion is expressed as the number of colony forming units (CFU) recovered from the monolayer divided by the number of CFU inoculated onto the monolayer multiplied by 100.

TABLE 3

Effect of Temperature on ADHESION to INT-407 Cells by *C. jejuni* Grown Conventionally (BHI) or According to Methods of the Present Invention (ENHANCED)

| Temperature | BHI (% adhesion) | ENHANCED (% adhesion) |
|---|---|---|
| 37° C. | 5.5 | 62.3 |
| 42° C. | 5.5 | 11.2 |

TABLE 4

Adhesion (FOLD INCREASE) to INT-407 by Different Strains of *C. jejuni* Grown Conventionally (BHI) or According to Methods of the Present Invention (ENHANCED)

| Strain | BHI | ENHANCED |
|---|---|---|
| 81-176 | 1.0 | 8.4 |
| 81-116 | 1.0 | 12.5 |
| HC | 1.0 | 28.2 |

In invasion assays, epithelial cells were grown and prepared according to the methods described above for the adhesion assay. Bacteria grown conventionally or according to methods of the present invention were added to the epithelial cells at a multiplicity of infection of 10 bacteria per cell to avoid saturation. The number of bacteria inoculated into the tissue culture well was calculated by plate counting. Following 2 h infection under 5% $CO_2$ for Campylobacter, and 30 min for Shigella, the infecting bacteria were aspirated off, and the monolayer was overlaid with growth medium containing gentamicin to kill any extracellular bacteria. Any culturable bacteria remaining at this point have invaded the epithelial cell monolayer. The incubation continued under $CO_2$ for 3 h in the case of *C. jejuni* infected cells, and 1.5 h for Shigella infected cells. Monolayers were washed with HBSS to remove gentamicin, and lysed by the addition of 0.1% deoxycholate. Bacteria in the lysates were enumerated by plate counting and percent invasion was expressed as the number of gentamicin resistant bacteria compared to the number of inoculum bacteria.

Invasion is expressed as the percent of cell entering the monolayer, as determined by the number of colony forming units (CFU) recovered from the monolayer after gentamycin treatment divided by the number of CFU inoculated onto the monolayer multiplied by 100.

The effect of temperature on invasion of INT-407 cells by *C. jejuni* 81-176 grown conventionally or according to the methods of Example 5 above is shown in Table 5 below.

Differences in invasion of INT-407 cells by several strains of *C.jejuni* grown conventionally or according to methods of the present invention are shown in Table 6 below.

The effect of DOC on adhesion to and invasion into INT-407 cells by *C. jejuni* 81-176 grown conventionally or according to the methods of Example 5 above is shown in Table 7 below.

The effect of DOC on adhesion to and invasion into INT-407 cells by Shigella grown conventionally or according to the methods of Example 5 above is shown in Table 8 below.

TABLE 5

Effect of Temperature on INVASION of INT-407 Cells by *C. jejuni* 81-176 Grown Conventionally (BHI) or According to Methods of the Present Invention (ENHANCED)

| Temperature | BHI (% invaded) | ENHANCED (% invaded) |
|---|---|---|
| 37° C. | 2.5 | 49.5 |
| 42° C. | 4.0 | 7.1 |

TABLE 6

INVASION (FOLD INCREASE) into INT-407 Cells by Different Strains of *C. jejuni* Grown Conventionally (BHI) or According to Methods of the Present Invention (ENHANCED)

| Strain | BHI | ENHANCED |
|---|---|---|
| 81-176 | 1.0 | 9.2 |
| 81-116 | 1.0 | 10.0 |
| HC | 1.0 | 26.7 |

TABLE 7

Effect of DOC Concentration on Adhesion and Invasion of INT-407 by *C. jejuni* 81-176 Grown Conventionally (BHI) or According to Methods of the Present Invention (ENHANCED)

| Treatment | Adhesion (%) | Invasion (%) |
|---|---|---|
| BHI | 9.3 | 6.3 |
| ENHANCED; 0.025% DOC | 18.3 | 17.4 |
| ENHANCED; 0.1% DOC | 52.6 | 37.0 |

TABLE 8

Effect of DOC on *S. flexneri* Invasion (Percent) or Adhesion (Percent) to INT-407 Cells Grown Conventionally (BHI) or According to Methods of the Present Invention (ENHANCED)

| Characteristic | BHI | ENHANCED |
|---|---|---|
| Adhesion | 1.0 | 140.0* |
| Invasion | 1.0 | 94.4 |

*More than the initially added bacteria were recovered due to growth of the bacteria during the assay Adhesion to and invasion of cultured INT-407 cells by several human isolates of *C. jejuni* (i.e., 81-116, 81-176 and HC) was greatly enhanced by addition of bile or deoxycholate to the culture medium (See Tables 4 and 6). The most effective dose of DOC was 0.1% (Table 7). The greatest response was obtained at 37° C., but not at 42° C. (the temperature at which Campylobacter is conventionally grown) (Tables 3 and 5).

Similar findings were made with *Shigella flexneri* (Table 8). Shigella grown according to the methods of the present invention had greatly enhanced abilities of both adhesion and invasion.

These data show methods of the present invention enhance invasion and adhesion of enteric pathogens.

Example 29

A rapid slide agglutination assay was used to show immuno-cross reactivity. *C. jejuni* strains grown conventionally or according to the methods of the present invention as exemplified in Example 5 were exposed to serum IgG from animals immunized with *C. jejuni* 81-176 (Lior 5) grown either conventionally, or according to the present invention (e.g., Example 5). The IgG antibodies were immobilized on Protein A coated latex beads. If there are cross reactive epitopes between the test serotype and the antibodies generated against the Lior 5 serotype, then nearly immediate clumping (i.e. agglutination) of the cells is visible. This clumping is rated based on a scale of 0 to 3 after allowing the reaction to proceed for a short period of time, where 0 means no observable clumping and 3 means a high degree of agglutination. The results of four strains are presented in Table 9 below.

TABLE 9

Cross Reactivity of Lior Serotypes Grown Conventionally (BHI) or According to Methods of the Present Invention (ENHANCED)

| CULTURE | GROWTH CONDITIONS | BEADS | REACTIVITY |
| --- | --- | --- | --- |
| 81-176 (L5) | BHI | Anti-BHI[a] | 1 |
| " | " | Anti-ENH[b] | 2 |
| " | ENHANCED | Anti-BHI | 2 |
| " | " | Anti-ENH | 2.5 |
| L2 | BHI | Anti-BHI | 1 |
| " | " | Anti-ENH | 1.5 |
| " | ENHANCED | Anti-BHI | 0 |
| " | " | Anti-ENH | 1.5 |
| L8 | BHI | Anti-BHI | 2 |
| " | " | Anti-ENH | 1 |
| " | ENHANCED | Anti-BHI | 1 |
| " | " | Anti-ENH | 2.5 |
| L21 | BHI | Anti-BHI | 0 |
| " | " | Anti-ENH | 2 |
| " | DOC | Anti-BHI | 0 |
| " | " | Anti-ENH | 2 |
| Media | BHI | Anti-BHI | 0 |
| " | " | Anti-ENH | 0 |

[a]Antibodies induced by 81-176 grown conventionally
[b]Antibodies induced by 81-176 grown according to methods of the present invention as exemplified in Example 5

Table 9 shows all four of the tested Lior serotypes (L5, L2, L8, L21) cross-reacted with antibody generated from animals immunized with enhanced *C. jejuni* 81-176 Lior serotype L5. Mucus lavage from the intestines of rabbits infected with *C. jejuni* 81-176, comprising IgA, reacted with eight out of the 10 major clinical serotypes (i.e., human pathogens) of *C. jejuni* grown according to methods of the present invention cross reacted with antibodies to Lior 5 serotype strain (see Table 16 below). The results show that methods of the present invention significantly extend the number of Lior serotypes which cross react with anti-serum from animals immunized with Lior 5 serotype strain of *C. jejuni*.

Also, several species of Shigella grown according to methods of the present invention, but not those grown conventionally, cross react with IgG antibodies from animals immunized with *Shigella flexneri* 2457T grown with DOC.

8 EXAMPLES

VACCINE EFFICACY

Example 30

The ferret model for studying Campylobacter pathogenesis can be used as a model to evaluate vaccine efficacy in protecting against colonization and/or disease because infection of ferrets reproducibly generates two of the three disease manifestations seen in humans.

Twenty-four 7-to 9-week-old male ferrets were immunized orally with either PBS (as control), or formalin-fixed *C. jejuni* strain 81–176 grown conventionally (BHI) or according to methods of Example 5 (ENHANCED). Serum was isolated to determine baseline IgG titres. All vaccines and PBS were administered in the presence of the adjuvant LT, two times, one week apart (Day 0 and day 7, "vaccination"). Serum was collected one week later (day 14) ("post-vaccination") to determine IgG antibody titres. Four weeks post-vaccination (challenge), the ferrets were anesthetized with ACE promazineKetamine and challenged orally with a 10 ml PBS solution containing live *C. jejuni* 81–176 ($1\times10^{10}$ CFU). Thereafter the animals were monitored daily for mucoid diarrhea, bacteremia, fecal shedding of Campylobacter, weight changes, occult blood, and fecal leukocytes. Bacteremia was detected by drawing 1 to 2 ml of blood from the jugular vein of anesthetized ferrets and incubating the specimen in a vented trypticase soy broth culture. Subcultures to blood agar plates were taken at 2, 5 and 7 days post challenge. Serum samples were collected prior to immunization (baseline), one week after the second immunization, and at the time of challenge, and one week post challenge to determine IgG titres.

Occult blood was detected by testing fecal material on a Hemacult card. Fecal material was smeared on a slide and stained with methylene blue to detect fecal leukocytes. Fecal shedding of Campylobacter was established by culturing smears from rectal swabs on Campylobacter-selective medium plates (trypticase soy agar, 5% sheep blood, trimethoprim, vancomycin, polymyxin B, cephalothin, and amphotericin B, Remel, Lenexa, KS). Results from these experiments are presented in Tables 10 and 11 below.

TABLE 10

Vaccination Protects Against *C. jejuni* 81-176 in Ferrets

| VACCINE | POSITIVE COLONIZATION DAY 5 POST-CHALLENGE[a] | DISEASE[b] |
|---|---|---|
| PBS | 6/6 | 1/6 |
| BHI | 0/6 | 2/6 |
| ENHANCED | 0/5[c] | 0/6 |

[a]Number positive colonization/number tested
[b]Presented with green mucus/unformed/watery stools
[c]One animal died in the group after disease state was determined but before colonization was scored

TABLE 11

Ferret Sera IgG Geometric Mean Titer

| Group | Baseline | One week post-vaccine | At challenge | One week post challenge |
|---|---|---|---|---|
| PBS | 6.4 | 4.9 | 6.4 | 1380.4 |
| BHI | 6.4 | 94.0 | 94.0 | 26505.3 |
| ENHANCED | 6.8 | 234.4 | 1621.8 | 56234.1[a] |

[a]Mean titre for the five surviving animals

Table 10 shows that upon live challenge, animals immunized with a killed-whole cell vaccine of the present invention were protected against colonization and disease. The data in Table 11 show that a much greater IgG antibody titre results from vaccines of the present invention (ENHANCED) than from enteric bacteria grown conventionally (BHI).

These results demonstrate that immunogenicity (Table 11) and protection from infection (Table 10) was obtained with vaccines of the present invention and was greater than that seen when animals were vaccinated with bacteria grown conventionally. Therefore bacteria produced by the methods of the present invention are useful as vaccines to protect mammals from infection.

Example 31

Mice do not naturally develop Campylobacter or Shigella infections as do ferrets, but they have been used by those skilled in the art to show resistance to intestinal colonization upon oral challenge of immunized animals or resistance to illness via lung infection of immunized animals. The mouse intranasal inoculation model then can be used to predict the efficacy of vaccines for use in other animals or humans. This assay was described by Mallet, et al. (*Vaccine*, 11:190–196, 1993).

Groups of 10 female Balb/c mice about sixteen weeks old were immunized orally with phosphate-buffered saline (PBS) *C. jejuni* conventionally grown (BHI) or *C. jejuni* grown according to Example 5 (ENHANCED) in doses of about $10^7$ CFU or $10^9$ CFU, then challenged. IgA titres from intestinal mucus in each group were determined by ELISA methods and are presented in Table 12 below.

TABLE 12

IgA Responses After Oral Immunization with ($10^7$ or $10^9$) Campylobacter Whole Cell Vaccines in Mice

| Immunization | Lavage IgA Titre[a] | % Responders[b] |
|---|---|---|
| PBS | 23 | 14 |
| ENHANCED ($10^7$) | 114 | 75 |
| ENHANCED ($10^9$) | 78 | 75 |
| BHI ($10^7$) | 40 | 25 |
| BHI ($10^9$) | 32 | 12 |

[a]Lavage titre indicates the mean anti-*C. jejuni* IgA titre obtained for each individual group of mice.
[b]Responders are defined as those animals whose endpoint titres exceeded 2 standard deviations above the mean of the animals receiving PBS alone Table 12 shows that animals immunized with bacteria grown according to the methods of the present invention have a higher intestinal IgA antibody titre as presented by a greater percentage of responders than animals immunized with bacteria grown conventionally.

9 EXAMPLE

MECHANISM OF ANTIGENIC ALTERATION OR ENHANCEMENT BY DOC

Example 32

Although not intending for the present invention to be limited to any particular mechanism of action, the present inventors have obtained evidence that suggests that deoxycholate (DOC) appears to have a two fold action in altering or enhancing the antigenicity of enteric bacteria. Evidence indicates that one aspect of DOC's effect is mediated through calcium dependent effects, as DOC binds calcium and thus lowers the calcium concentration in the medium. The evidence is as follows. When *C. jejuni* 81–176 is cultured with the membrane permeable calcium chelator BAPTA/AM and without DOC, its invasiveness of INT-407 cells is enhanced approximately 10-fold (see Table 13 below). BAPTA/AM treatment alone, however, does not enhance the immuno-cross reactivity of *C. jejuni* 81–176 cells.

The results shown in Table 13 were obtained using *C. jejuni* 81–176 cultured according to the protocol described in Example 5 except that 25 μM BAPTA/AM was substituted for 0.1% DOC. The invasion assays were carried out and scored as described in Example 28 in Section 7 above.

TABLE 13

Invasion of INT-407 Cells by *C. jejuni* Grown Conventionally (BHI) or with BAPTA/AM

| | Culture condition | |
|---|---|---|
| Strain | BHI | BAPTA/AM |
| *C. jejuni* 81-176 | 3.0 | 36.9 |

Several bacterial genera that are susceptible to antigenic enhancement or alteration by bile or bile salts such as DOC (e.g., Campylobacter, Shigella, Helicobacter) have genes homologous to low calcium response (lcr) genes from Yersinia. The lcr locus is known to regulate virulence of Yersinia in response to low calcium levels. Two Campylobacter genes involved in flagellin expression and assembly which are required for invasion (flaA, flbA) are regulated in part by the lcr product. Analysis of the behavior of Campylobacter flaA and flbB mutants grown conventionally or under virulence enhancing conditions of the present invention show that invasion, but not Congo red dye binding or increased cross-reactivity, is calcium dependent (see Table 14 below).

The results shown in Table 14 were obtained using *C. jejuni* cultured conventionally or according to the methods of the present invention as exemplified in Example 5. The invasion assays were carried out and scored as described in Example 28 above.

TABLE 14

Invasion of INT-407 Cells by *C. jejuni* Mutants Grown Conventionally (BHI) or According to Methods of the Present Invention (ENHANCED)

| | Culture condition | |
|---|---|---|
| Strain | BHI | ENHANCED |
| *C. jejuni* 81-176 | 3.5 | 40.8 |
| *C. jejuni* flaA | 0.05 | 0.05 |
| *C. jejuni* flbA | 0.01 | 0.04 |

The *C. jejuni* fla and flbA mutants do exhibit significantly enhanced Congo red binding and immuno-cross reactivity when cultured with DOC (see Table 15 and FIG. 6, respectively). The results shown in Table 15 and FIG. 6 were obtained using *C. jejuni* cultured conventionally or according to the methods of the present invention as exemplified in Example 5 above. The Congo red dye binding assays, whose results are shown in Table 15, were carried out as described in Example 26 above. The immuno-cross reactivity, whose results are shown in FIG. 6, were carried out as described in Example 29 above.

TABLE 15

Congo Red Dye Binding by *C. jejuni* Mutants
Grown Conventionally (BHI) or
According to Methods of the Invention (ENHANCED)

| Strain | Culture condition | |
|---|---|---|
| | BHI | ENHANCED |
| *C. jejuni* 81-176 | 0.07 | 1.68 |
| *C. jejuni* flaA | 0.10 | 1.60 |
| *C. jejuni* flbA | 0.12 | 0.80 |

The flaA mutant is unable to express flagellin. The flaA mutant and a flaA-flaB double mutant (received from C. Grant, NIH) are both noninvasive even after treatment with DOC, indicating that flagellin is required for invasion. Interestingly, the normally exhibited (i.e., non-DOC induced) immuno-cross reactivity observed between the isogenic parent strain of these fla mutants and certain other Lior serotypes of *C. jejuni* is absent in the mutants. However, DOC treatment can induce these flagellin-less mutants to exhibit enhanced immuno-cross reactivity and Congo red binding.

These findings indicate that DOC regulates virulence functions in enteric bacteria via calcium-dependent (e.g., invasiveness) and calcium-independent (e.g., Congo red dye binding) mechanisms. These findings further suggest that enhanced immuno-cross reactivity and Congo red binding induced by DOC is at least in part flagellin-independent.

10 EXAMPLE

DOC INDUCES ENHANCED SEROTYPE AND SPECIES IMMUNO-CROSS REACTIVITY OF CAMPYLOBACTER JEJUNI

Example 33

The serotype immuno-cross reactivity of *Campylobacter jejuni* grown according the methods of the present invention was examined using the rapid slide agglutination assay. The assay used intestinal mucus from immunized and non-immunized rabbits to determine the effects of altering culture conditions on the cross-reactivity of heterologous strains of Campylobacter. The rabbits were immunized with live *C. jejuni* 81-176 grown conventionally. The agglutination activity of the mucus antibodies were tested against twenty-four Campylobacter strains, comprising eighteen serotypes, grown conventionally in BHI-YE medium or according to the methods of the invention as exemplified in Example 5.

The results of the agglutination assays show that the cross-agglutination of heterologous Campylobacter strains was broader and, in many cases, stronger when the strains were grown according to the methods of the invention than when they were grown conventionally. Specifically, there was an over two fold increase in heterologous agglutination reactivity: 6 of 24 conventionally-grown heterologous strains agglutinated at level + or greater in the anti-81–176 immune mucus, whereas 14 of the same 24 strains grown under DOC conditions agglutinated at level + or greater. Further, while eighteen of the heterologous strains demonstrated weak (±) or no agglutination when conventionally grown, eleven of these same strains showed an enhanced agglutination response when grown under ENHANCED culture conditions (e.g., DOC containing medium).

Table 16 illustrates cross-reactivity of anti-81–176 immune rabbit mucus against 19 heterologous Lior serotypes consisting of 22 strains grown conventionally (BHI-YE) or using the methods of Example 5 (ENHANCED). Even though this experiment assayed only a fraction of the known Lior serotypes, the results demonstrate that the methods of the invention induce substantial immuno-cross reactivity between Lior serotypes. The results further show that the DOC enhanced or induced antigens in Campylobacter appear to be important in the secretory IgA response associated with resistance to and recovery from intestinal infection by Campylobacter.

It should be further noted that strains of Lior serotype 8 are of a different species, *Campylobacter coli*. One of the 2 strains (VC167) of this serotype strongly agglutinated (3+) in anti-81–176 immune rabbit mucus. This result indicates that a vaccine derived from a *C. jejuni* strain (e.g., Lior 5), not only can cross-protect against heterologous serotypes within the same species, but also other Campylobacter species (e.g., *Campylobacter coli*). Also worth noting is that Lior serotypes 1, 2, 4, 9, and 11 are among the most prevalent disease-associated serotypes world-wide. They all demonstrated detectable cross-reactivity in this assay.

TABLE 16

Agglutination Response of 20 Campylobacter Serotypes Grown
Conventionally (BHI-YE) or According to the Methods of the Invention
(ENHANCED) to Non-immune[b] or Anti-81-176[a] Immune Rabbit Mucus

| | | Agglutination response[c] | | | |
|---|---|---|---|---|---|
| | Lior | Non-immune mucus | | Immune Mucus | |
| Strain | Serotype | BHI-YE | ENHANCED | BHI-YE | ENHANCED |
| 134 | 1 | – | – | – | ++ |
| 195 | 2 | – | – | – | ± |
| 1 | 4 | – | – | – | +++ |
| 170 | 5 | – | – | +++ | ++++ |
| 81–176 | 5 | – | – | ++++ | ++++ |
| 6 | 6 | – | – | ++++ | +++ |
| 81–116 | 6 | – | – | + | ++ |
| 35 | 7 | – | – | – | + |
| 52 | 8 | – | + | + | ++ |
| VC-167 | 8 | – | – | + | +++ |
| VC-159 | 8 | – | – | ± | – |
| 88 | 9 | – | – | – | ± |
| 244 | 11 | – | – | ± | +++ |
| 556 | 17 | – | – | + | – |
| 563 | 18 | – | – | – | – |
| 544 | 19 | – | ++ | – | ++ |
| 699 | 21 | – | – | ± | ++ |
| 1180 | 28 | – | – | + | +++ |
| 1982 | 29 | – | – | – | – |
| 910 | 32 | – | ++ | – | ++ |
| 2074 | 36 | – | – | – | – |
| HC | 36 | – | + | – | + |
| 2984 | 46 | – | – | – | – |
| 79171 | 72 | – | – | – | – |

[a]The anti-81-176 mucus were obtained from rabbits infected with live *C. jejuni* 81-176 grown conventionally
[b]The non-immune mucus were obtained from uninfected rabbits
[c]The agglutination responses range from negative (–), to very weak (±), to very strong (++++)

11 EXAMPLE

ADDITIONAL EXPERIMENTS OF VACCINE EFFICACY OF CAMPYLOBACTER

Example 34

The protective efficacy of formalin-fixed whole cell *Campylobacter jejuni* grown according to the methods of the present invention was determined using the mouse colonization model reported by Baqar (*Infect. & Immun.*, 63:3731–3735, 1995).

C. jejuni 81-176 was grown and harvested according to Example 5 and inactivated with 0.075% formalin as described above. Groups of five 6 to 8 week old female Balb/c mice were administered three oral doses (0.25 ml/dose in endotoxin-free PBS) containing either $10^5$, $10^7$, or $10^9$ inactivated bacterial particles alone or in combination with 25 μg of the heat labile enterotoxin from E. coli (LT). Doses were given at 48 hour intervals and immediately after two 0.5 ml doses of 5% sodium bicarbonate solution (pH 8.5) were given at 15 minute intervals, to neutralize gastric acidity. As controls, groups of animals were vaccinated with PBS alone or in combination with the LT adjuvant. Approximately 28 days after administration of the third dose, vaccinated animals were challenged either nasally or orally with approximately $10^8$ colony forming units (CFU) of live conventionally grown C. jejuni 81-176. The duration of intestinal colonization was determined by monitoring fecal shedding every day over a 9 day period. Fecal material was emulsified in sterile PBS and aliquots plated on Campylobacter blood agar. Plates were incubated at 35° C. under microaerophillic conditions (Campylobacter GasPak, BBL) for 3–5 days to allow growth of C. jejuni. Colonization results are expressed as the percentage of animals shedding Campylobacter organisms on a given sample day.

As shown in FIG. 7, all nasally challenged animals, both immunized and control, shed organisms immediately after challenge (day 1). Eighty to one hundred percent of the control animals remained colonized for 9 days after challenge. In contrast, significantly fewer animals in the vaccinated groups shed organisms during the course of the 9 day assay period. Both the degree of and time to clearance of challenge organisms were dependent on the amount of vaccine administered. The low ($10^5$ particles/dose) and intermediate vaccine doses ($10^7$ particles/dose) gave a gradual and incomplete rate of clearing. The presence of adjuvant increased the degree of protection at these doses. Surprisingly, at the highest dose tested ($10^9$ particles/dose) the non-adjuvantized vaccine produced a level of protection equal to or slightly greater than that obtained when a comparable dose was administered with the LT adjuvant.

Similar results were obtained when orally vaccinated animals were subsequently challenged orally (see FIG. 8). These results indicate that immunization with inactivated Campylobacter grown according to the methods of the present invention affords protection against subsequent challenges of live Campylobacter and the immunization is efficacious even when administered orally without the use of an adjuvant.

The protective efficacy of formalin-fixed whole cell Campylobacter jejuni grown according to the methods of the present invention (see, e.g., Example 5) administered intraperitoneally (IP) was also evaluated. For these experiments, groups of 20 female Balb/c mice were administered a single dose of 1.3×$10^{10}$, 2.5×$10^9$,5. 0×$10^8$, 1.0×$10^8$ or 2.0×$10^7$ inactivated C. jejuni particles in 0.5 ml endotoxin-free PBS without adjuvant. The animals were challenged 14 days later with a single lethal dose of live C. jejuni 81–176 (approximately 1.0×$10^{10}$ CFU in endotoxin-free PBS) delivered intraperitoneally. Animals were monitored daily for 4 days for mortality.

As shown in Table 17, a single intraperitoneal dose of 5.0×$10^8$ inactivated C. jejuni particles induced an immunologcal response sufficient to protect animals against a live C. jejuni challenge.

TABLE 17

Protection Afforded By IP Delivered V2Inactivated C. jejuni Prepared According to the Methods of the Present Invention

| Dose | Mortality Day | | | | Survivors |
|---|---|---|---|---|---|
| | 1 | 2 | 3 | 4 | |
| 1.3 × $10^{10}$ | 0 | 4 | 0 | 0 | 16 |
| 2.5 × $10^9$ | 0 | 0 | 0 | 0 | 20 |
| 5.0 × $10^8$ | 0 | 0 | 0 | 0 | 20 |
| 1.0 × $10^8$ | 11 | 7 | 0 | 0 | 2 |
| 5.0 × $10^7$ | 10 | 6 | 2 | 0 | 2 |
| PBS Control | 4 | 3 | 2 | 0 | 1 |

12 EXAMPLES

DOC ENHANCED INVASIVENESS, CONGO RED BINDING AND IMMUNO-CROSS REACTIVITY OF SHIGELLA

Example 35

The invasiveness of Shigella sp. grown in vitro is affected by the culture's growth phase. The invasiveness of Shigella flexneri 2457T cells grown conventionally (BHI), or according to the methods of the invention as exemplified by Example 9 (DOC-EL) (wherein the cells are from an early log phase culture), or according to Example 9 but allowing the culture to reach late log phase before harvesting the cells (DOC-LL) was tested according to the procedures described in Example 28. The results show that culturing with DOC enhances invasiveness and that the maximum enhancement is achieved during early log phase of growth (see FIG. 9).

Culturing with DOC according to the methods of the invention also enhances the invasiveness of other Shigella species, S. sonnei, and S. dysentariae (see FIG. 10). In polarized epithelial cells the enhanced invasiveness of Shigella was observed only when the epithelial cells were infected basolaterally by the bacteria. This finding is consistant with the invasion process observed in vivo.

Comparitive studies show that Shigella grown according to the methods of the present invention are nearly 10-fold more invasive than Shigella prepared according to the procedure described by Pope et al. (Infect. & Immun., 63:3642-3648 1995).

Example 36

Shigella cultured according to the methods of the present invention also exhibit enhanced Congo red binding. S. flexneri 2457T and S. sonnei grown conventionally (BHI) or according to the methods of the present invention as exemplified in Example 9 were assayed for their dye binding abilities using procedures described in Example 26 above. The results show that growth in DOC enhanced Congo red binding by the two Shigella species 10 to 20 fold (see Table 18)

TABLE 18

Congo Red Binding by S. flexneri and S. sonnei
Grown Conventionally (BHI) or
According to Methods of the Present Invention (ENHANCED)

| Strain | Culture condition | |
|---|---|---|
| | BHI | ENHANCED |
| S. flexneri 2457T | 0.04 | 0.44 |
| S. sonnei | 0.02 | 0.40 |

Shigella is divided into four species and various serotypes. The immuno-cross reactivity of Shigella flexneri grown according the methods of the present invention was examined using the agglutination assay as described in Example 28. The assay used antiserum from immunized rabbits to determine the effects of culture conditions on the immuno-cross reactivity of different Shigella species. The rabbits were immunized with formalin-fixed Shigella flexneri 2457T grown according to the methods of Example 9. The agglutination activity of the IgG antibodies obtained from the immunized animals were tested against all four Shigella species grown conventionally in BHI medium or according to the methods of the invention (e.g., Example 9). The results of the agglutination assays show that growth with DOC significantly enhanced the agglutination activity of the homologous Shigella flexneri as well as those of the three heterologous Shigella species to anti-S. flexneri antibody (see FIG. 11).

13 EXAMPLE

VACCINE EFFICACY OF SHIGELLA

Example 37

The protective efficacy of formalin-fixed whole cell Shigella flexneri grown according to the methods of the present invention was determined using the mouse nasal challenge model developed by C. P. Mallett et al. (Vaccine, 11:190–196, 1993). Briefly, Shigella flexneri was grown and harvested according to the methods exemplified in Example 9 and inactivated with 0.075% formalin as described in Example 30. Approximately $10^7$ inactivated bacterial particles were used to vaccinate 14–16 week-old female Balb/c mice. The inactivated S. flexneri was suspended in sterile, endotoxin-free PBS at a concentration of $10^8$ particles/ml and 35 µl of this material was administered nasally to groups of 10 lightly anesthetized animals. A total of three immunizations were given at 14 day intervals.

To test the effect of an adjuvant on the protective ability of the Shigella whole cell vaccine, groups of animals were immunized using a suspension that contained the inactivated vaccine and 5 µg of the heat-labile enterotoxin from E. coli (LT). Fourteen days after the third immunization, animals were challenged nasally with a sublethal wasting dose ($10^5$ cfu) of either live S. flexneri or S. sonnei. Immediately before and at 1, 2, 5, and 7 days following the challenge, animals were weighed and the mean group weight determined. Results are shown in Table 19.

TABLE 19

Inactivated Shigella flexneri Whole Cell Vaccine Protects Mice
Against Nasal Challenge With Live S. flexneri or S. sonnei

| Challenge organism | Vaccination | Percent Weight Change Post Challenge | | | |
|---|---|---|---|---|---|
| | | Day 1 | Day 2 | Day 5 | Day 7 |
| S. flexneri | PBS | −8.1 | −18.2 | −17.7 | −18.3 |
| | vaccine | −5.4 | −2.9 | −2.5 | −1.6 |
| | vaccine + adjuvant | −7.0 | −2.0 | −1.5 | 1.5 |
| S. sonnei | PBS | −8.1 | −17.5 | −9.3 | −6.4 |
| | vaccine | −6.7 | −11.3 | −6.5 | −6.0 |
| | vaccine + adjuvant | −6.4 | −5.2 | −1.3 | −2.1 |

Ten mice in each group were immunized 3× nasally with vaccine comprsing $10^7$ inactivated S. flexneri grown according to Example 9

The mice immunized with vaccine comprising inactivated S. flexneri grown according to the methods of the invention were protected against challenge with live S. flexneri organisms. Those mice suffered less weight loss and underwent more rapid weight recovery as compared to unvaccinated mice, i.e. the PBS sham control group. Surprisingly, the S. flexneri vaccine also protected the mice against challenge with live S. sonnei. Interestingly, animals receiving the vaccine alone without the LT adjuvant were as well protected against the homologous S. flexneri challenge as animals that received the adjuvantized vaccine. The S. flexneri vaccine alone also conferred protection to heterologous challenges by S. sonnei. The inclusion of the LT adjuvant, however, noticibly enhanced the protection against the challenge by S. sonnei. These findings indicate that vaccine comprising inactivated Shigella prepared according to the methods of the invention is effective in a recognized Shigella disease model and does not require an adjuvant in preventing or attenutating various Shigella infections.

14 EXAMPLE

FACTORS THAT AFFECT THE ADHESIVENESS OF H. PYLORI TO ANIMAL CELLS

Example 38

The adherence of H. pylori is enhanced by growth in glycocholate or bile. Cells of H. pylori strain NB3-2 or G1–4 were added to BHI broth plus 4% bovine calf serum. After inoculation the flasks were flushed with 10% $CO_2$-5%$O_2$-85% $N_2$ and incubated for 22 h at 37° C. with shaking. After this incubation, the culture was diluted 1 to 10 to a flask containing 1 liter of the BHI medium with 4% bovine calf serum containing various concentrations of bovine bile (0.025% to 0.2%). These cultures were again flushed with the same gas mixture, and incubated at 37° C. The cells were harvested at various times up to 18 h and their adherence to INT-407 cells assayed using the methods described in Example 28. The results show that culturing with bile enhanced the adhesiveness of H. pylori to INT-407 cells (see FIGS. 12 and 13). For the NB3-2 strain, peak adhesiveness, a 4 to 6 fold increase over that of non-enhanced culture, occurred after about 8 h of growth (FIG. 12). For the G1–4 strain, peak adhesiveness, a 2 to 3 fold increase over that of none-enhanced culture, occurred between 12–14 h of growth in 0.2% bile (FIG. 13). These "peak" times generally corresponded to the period when the culture of each strain was in log phase growth.

15 EXAMPLE

VACCINE EFFICACY OF HELICOBACTER GROWN ACCORDING TO THE METHODS OF THE PRESENT INVENTION

Example 39

The protective efficacy of formalin-fixed whole cell *Helicobacter pylori* grown according to the methods of the present invention was determined using the mouse *Helicobacter felis* gastric colonization model described by Chen et al. (*Lancet*, 339:1120–1121, 1992). *Helicobacter pylori* strain G1–4 was grown as a seed culture for about 22 h at 37° C. under 10% $CO_2$, 90% air in BHI media containing 4% bovine calf serum. An aliqout of this culture was used to inoculate a 10-fold volume of the same media containing 0.1% (v/v) bovine bile. After 12–14 h of growth at 37° C., the cells are harvested by centrifugation and resuspended in 1/10 of the original volume of Hank's Balanced Salts Solution (HBSS) at room temperature. Cells were recentrifuged and again suspended in 1/100 of the original volume of HBSS. To the buffered cell suspension, formalin was added to a concentration of 0.075% and the cells inactivated by stirring the suspension at room temperature for 6 h then cooling the solution at 4° C. for 18 hours.

Protection potential was routinely measured by administering 3 doses of this inactivated whole cell vaccine orally to 6–8 week old female Balb/c Helicobacter-free mice at days 0, 7 and 14 or at days 0, 7 and 21. Doses of $10^9$ bacterial particles per dose were evaluated in combination with the heat labile enterotoxin of *E. coli*. Fourteen days after the third immunizing dose, animals were challenged orally with a single dose ($10^7$ CFU/dose) of live *H. felis*.

Two weeks after challenge the animals were sacrificed and antral stomach segments analyzed for urease activity to determine the presence of *H. felis*. Urease activity was determined by incubating antral tissue samples in 0.5 ml Stuart's Urease Broth (Remel) at room temperature for 4–24 hours. A color change from clear to red occuring within this period was taken as a positive urease result.

As shown in Table 20, administration of enhanced Helicobacter whole cell vaccine prepared using *H. pylori* strain G1–4 protected animals against an *H. felis* oral challenge.

TABLE 20

Protection Against Helicobacter Infections with Vaccines Comprising Inactivated *H. pylori* Grown According to Methods of the Present Invention

| Immunizing Agents[a] | Challenge Organisms ($10^7$ CFU) | Colonized/ Total | Percent Protection |
|---|---|---|---|
| Experiment 1 | | | |
| *H. pylori*[b] | *H. felis* | 4/13 | 71 |
| PBS + LT | *H. felis* | 9/9 | 0 |
| Experiment 2 | | | |
| *H. pylori*[b] | *H. felis* | 2/15 | 87 |
| PBS + LT | *H. felis* | 10/10 | 0 |

[a]All agents given with 10 µg LT (Labile toxin of ETEC) adjuvant as 3 oral doses at 7 day intervals
[b]Given as 1 × $10^9$ CFU of Strain G1-4 in a 0.25 ml dose Results of these experiments show the relevance of enhanced enteric bacterial properties to in vivo immunogenicity.

The methods of the present invention produce bacteria capable of inducing an immunogenic response which is protective and therefore are useful as vaccines.

16 DEPOSIT OF MICROORGANISM

The following microorganisms have been deposited with the American Type Culture Collection, 12301 Parklawn Drive, Rockville, Md. 20852, USA, and have the indicated accession numbers:

| Microorganism | Accession No. | Deposit Date |
|---|---|---|
| *Helicobacter pylori* NB3-2 | 55714 | September 29, 1995 |
| *Holicobacter pylori* G1-4 | 55713 | September 29, 1995 |

Other equivalents of the methods of the present invention may be easily determined by those skilled in the art and such equivalents are intended to be included by this invention. The foregoing disclosure includes all the information deemed essential to enable those skilled in the art to practice the claimed invention. Because the cited patents or publications may provide further useful information all the materials cited herein are hereby incorporated by reference in their entirety.

What is claimed is:

1. A method of growing Campylobacter bacteria having an enhanced antigenic property which comprises growing a culture of a Campylobacter species in vitro in a culture medium with a combination of conditions comprising:

a) about 0.05% to about 3% bile or about 0.025% to about 0.6% of one or more bile acids or salts thereof;

b) at a temperature between about 30° C. and about 42° C.;

c) in air or a gas mixture, wherein the gas mixture comprises i) about 5% to about 20% $CO_2$ with about 80% to about 95% air; or ii), about 5% to about 10% $O_2$ with about 10% to about 20% $CO_2$ with about 70% to about 85% $N_2$; and d) a divalent cation chelator selected from the group consisting of 0 to about 100 µM of 1,2-bis(2-aminophenoxy)ethane-N,N,N', N'-tetraacetic acid/acetoxymethyl ester, 0 to about 10 mM of ethylene-bis(oxyethylenenitrilo)-tetraacetic acid and 0 to about 100 µM of ethylene-bis(oxyethylenenitrilo)-tetraacetic acid/acetoxymethyl ester, for a sufficient time so that the culture is in a growth phase at about early log phase, between early log phase and stationary phase, or at about stationary phase, wherein the enhanced antigenic property is a higher level of an immunogenic antigen or a new immunogenic antigen when compared to the antigenic property of bacteria from a culture of the Campylobacter species grown in brain heart infusion broth.

2. The method according to claim 1, wherein said bile salt or acid comprises deoxycholate or deoxycholic acid.

3. The method according to claim 1, wherein said Campylobacter species is *Campylobacter jejuni* or *Campylobacter coli*.

4. The method according to claim 3, wherein said Campylobacter species is a *Campylobacter jejuni* strain selected from the group consisting of 134, 195, 170, 81–176, 6, 81–116, 35, 52, VC-167, 88, 244, 544, 699, 1180, 910, and HC.

5. The method of claim 3, wherein said *Campylobacter jejuni* is strain 81–176 and the combination of conditions comprises:

a) about 0.1% bile salt which is deoxycholate or about 0.8% bile;

b) the temperature is about 37° C.;

c) in about 10% to about 20% $CO_2$ and about 80% to about 90% air, and the culture is grown for a sufficient time so that the culture is in stationary phase.

6. A method of growing Campylobacter bacteria having an enhanced antigenic property which comprises growing a culture of a Campylobacter species in vitro in a culture medium with a combination of conditions comprising:

a) a divalent cation chelator selected from the group cosisitng of about 1.0 to about 25 µM of 1,2-bis(2-aminophenoxy)ethane-N,N,N',N'-tetraacetic acid/acetoxymethyl ester, about 0.5 to about 10 mM of ethylene-bis(oxyethylenenitrilo)-tetraacetic acid, and about 1 to about 100 µM of ethylene-bis(oxyethylenenitrilo)-tetraacetic acid/acetoxymethyl ester;

b) at a temperature between about 30° C. and about 42° C.; and c) in air or a gas mixture, wherein the gas mixture comprises i) about 5% to about 20% $CO_2$ with about 80% to about 95% air; or ii) about 5% to about 10% $O_2$ with about 10% to about 20% $CO_2$ with about 70% to about 85% for a sufficient time so that the culture is in a growth phase at about early log phase, between early log phase and stationary phase, or at about stationary phase, wherein the enhanced antigenic property is a higher level of an immunogenic antigen or a new immunogenic antigen when compared to the antigenic property of bacteria from a culture of the Campylobacter species grown in brain heart infusion broth.

7. A Campylobacter bacterium having an enhanced antigenic property, which is harvested from a culture of a Campylobacter species grown in vitro in a culture medium with a combination of conditions comprising:

a) about 0.05% to about 3% bile or about 0.025% to about 0.6% of one or more bile acids or salts thereof;

b) at a temperature between about 30° C. and about 42° C.;

c) in air or a gas mixture, wherein the gas mixture comprises i) about 5% to about 20% $CO_2$ with about 80% to about 95% air; or ii) about 5% to about 10% $O_2$ with about 10% to about 20% $CO_2$ with about 70% to about 85% $N_2$; and d) a divalent cation chelator selected from the group consisting of 0 to about 100 µM of 1,2-bis(2-aminophenoxy)ethane-N,N,N', N'-tetraacetic acid/acetoxymethyl ester, 0 to about 10 mM of ethylene-bis(oxyethylenenitrilo)-tetraacetic acid, and 0 to about 100 µM of ethylene-bis(oxyethylenenitrilo)-tetraacetic acid/acetoxymethyl ester, wherein said Campylobacter culture is in a growth phase at about early log phase, between early log phase and stationary phase, or at about stationary phase, and the enhanced antigenic property is a higher level of an immunogenic antigen or a new immunogenic antigen when compared to the antigenic property of bacteria from a culture of the Campylobacter species grown in brain heart infusion broth.

8. The Campylobacter bacterium according to claim 7, wherein said bile salt or acid comprises deoxycholate or deoxycholic acid.

9. The Campylobacter bacterium according to claim 7, wherein said Campylobacter species is *Campylobacter jejuni* or *Campylobacter coli*.

10. The Campylobacter bacterium according to claim 9, wherein said Campylobacter species is a *Campylobacter jejuni* strain selected from the group consisting of 134, 195, 170, 81–176, 6, 81–116, 35, 52, VC-167, 88, 244, 544, 699, 1180, 910, and HC.

11. The Campylobacter bacterium according to claim 10, wherein said *Campylobacter jejuni* is strain 81–176 and the combination of conditions comprises:

a) about 0.1% bile salt which is deoxycholate or about 0.8% bile;

b) the temperature is about 37° C.;

c) in about 10% to about 20% $CO_2$ and about 80% to about 90% air, and the Campylobacter culture is in stationary phase.

12. A Campylobacter bacterium having an enhanced antigenic property, which is harvested from a culture of a Campylobacter species grown in vitro in a culture medium with a combination of conditions comprising:

a) a divalent cation chelator selected from the group consisting of about 1.0 to about 25 µM of 1,2-bis(2-aminophenoxy)ethane-N, N, N', N'-tetraacetic acid/acetoxymethyl ester,0.5 about 10 mM of ethylene-bis(oxyethylenenitrilo)-tetraacetic acid, and about 1.0 to about 100 µM of ethylene-bis(oxyethyleneitrilo)-tetraacetic acid/acetoxymethyl ester;

b) at a temperature between about 30° C. and about 42° C.; and c) in air or a gas mixture, wherein the gas mixture comprises i) about 5% to about 20% $CO_2$ with about 80% to about 95% air; or ii) about 5% to about 10% $O_2$ with about 10% to about 20% $CO_2$ with about 70% to about 85% $N_2$, wherein said Campylobacter culture is at about early log phase, between early log phase and stationary phase, or at about stationary phase, and the enhanced antigenic property is a higher level of an immunogenic antigen or a new immunogenic antigen when compared to the antigenic property of bacteria from a culture of the Campylobacter species grown in brain heart infusion broth.

\* \* \* \* \*